United States Patent [19]

Hassler et al.

[11] Patent Number: 4,817,614

[45] Date of Patent: Apr. 4, 1989

[54] METHOD AND APPARATUS FOR ADAPTIVE FOCUSING IN A MEDICAL ULTRASOUND IMAGING APPARATUS

[75] Inventors: Dietrich Hassler, Uttenreuth; Heinz Eschenbacher; Wolfgang Haerer, both of Erlange, all of Fed. Rep. of Germany

[73] Assignee: Siemens Aktiengesellschaft, Berlin and Munich, Fed. Rep. of Germany

[21] Appl. No.: 87,046

[22] Filed: Aug. 19, 1987

[30] Foreign Application Priority Data

Aug. 20, 1986 [DE] Fed. Rep. of Germany ....... 3628220

[51] Int. Cl.⁴ ............................................. A61B 10/00
[52] U.S. Cl. .................................. 128/660.05; 73/625
[58] Field of Search .................. 128/660; 73/602, 597, 73/625, 645–648

[56] References Cited

U.S. PATENT DOCUMENTS

| | | | |
|---|---|---|---|
| 3,805,596 | 4/1974 | Klahr | 73/602 |
| 4,395,909 | 8/1983 | Steinberg et al. | 128/660 |
| 4,397,006 | 8/1983 | Galbraith, Jr. | 73/602 |
| 4,471,785 | 9/1984 | Wilson et al. | 128/660 |
| 4,484,477 | 11/1984 | Buxton | 73/626 |
| 4,592,237 | 6/1986 | Ogura et al. | 73/602 |
| 4,653,505 | 3/1987 | Iinuma | 128/660 |
| 4,691,570 | 9/1987 | Hassler | 128/660 |

FOREIGN PATENT DOCUMENTS

0068052 6/1981 European Pat. Off. .
0119844 9/1984 European Pat. Off. .

OTHER PUBLICATIONS

"Speckel Pattern Correlation with Lateral Aperture Translation: Experimental Results and Implications for Spatial Compounding," Trahey et al, IEEE Transactions on Ultrasonics, Ferroelectrics and Frequency Control, vol. UFFC-33, No. 3, May 1986, pp. 257–264.

"Active Incoherent Ultrasonic Imaging Through an Inhomogeneous Layer," Yokota et al, J. Acoust. Soc. Am. 77(1), Jan. 1985, pp. 144–152.

"Super-Resolution Ultrasonic Imaging by Using Adaptive Focusing," Yokota et al, J. Acoust. Soc. Am. 77(2), Feb. 1985, pp. 567–572.

"Adaptive Ultrasonic Array Imaging System Through an Inhomogeneous Layer," Hirama et al, J. Acoust. Soc. Am. 71(1), Jan. 1982, pp. 100–109.

"Backscatter and Attenuation Imaging from Ultrasonic Scanning in Medicine," Farrel, IBM J. Res. Develop., vol. 26, No. 6, Nov. 1982, pp. 746–758.

Primary Examiner—Francis J. Jaworski
Assistant Examiner—George Manuel
Attorney, Agent, or Firm—Hill, Van Santen, Steadman & Simpson

[57] ABSTRACT

A sectional plane of the examination subject is first scanned by focused ultrasound transmission beams in an adaptation phase. Disturbing effects from the reflected echo signals which are caused by the inhomogenities in the tissue are thereby measured. In this adaptation phase, correction values for the delay time of the signals of the elemental transducers of the ultrasound array in comparison to the standard focusing are also derived from the measured values. In a following B-image imaging phase, the delay times of the active aperture are then varied dependent on the correction values during the emission and/or during reception. The disturbing effects are thereby compensated. A method and apparatus are disclosed which are especially well-suited for linear array systems and for patients having inhomogeneous tissues.

20 Claims, 19 Drawing Sheets (1) $\quad \sum_{i=1}^{6}[\tau_{1i}-(\tau_{2i}+c_2)]^2 = \text{Min for } c_2$ (2) $\quad \bar{\tau}_{j1} = \dfrac{\tau_{1i}+\tau_{2i}+c_2}{2} \longrightarrow \bar{\tau}_{11}=\bar{\tau}_2$ (3) $\quad \sum_{i=2}^{7}[\bar{\tau}_{j1}-(\tau_{3i}+c_3)]^2 = \text{Min for } c_3$ (4) $\quad \bar{\tau}_{j2} = \dfrac{2\bar{\tau}_{j1}+\tau_{3i}+c_3}{3} \longrightarrow \bar{\tau}_{21}=\bar{\tau}_3$ (5) $\quad \sum_{i=3}^{8}[\bar{\tau}_{j2}-(\tau_{4i}+c_4)]^2 = \text{Min for } c_4$ (6) $\quad \bar{\tau}_{j3} = \dfrac{3\bar{\tau}_{j2}+(\tau_{4i}+c_4)}{4} \longrightarrow \bar{\tau}_{31}=\bar{\tau}_4$

FIG 10

METHOD AND APPARATUS FOR ADAPTIVE FOCUSING IN A MEDICAL ULTRASOUND IMAGING APPARATUS

BACKGROUND OF THE INVENTION

1. Field of the Invention

The present invention is directed to a method and apparatus for obtaining an ultrasound image of an examination subject having image-disturbing inhomogeneities, and in particular to a method and apparatus wherein the disturbances caused by the inhomogeneities are substantially compensated so that the resulting image is free of artifacts.

2. Description Of The Prior Art

Attempts have been made in B-image scanners to achieve a high lateral resolution by employing applicators (ultrasound arrays) having extremely large active apertures (usually in reception). This goal has been achieved in the case of homogeneous phantoms and in some of the examined patients. The clarity and resolution of ultrasound B-images from living tissue, however, is frequently noticibly less than that from phantoms A not negligibly low percentage of patients is so inhomogeneous in sound-physical terms that no gains can be acquired from the large aperture. The corresponding ultrasound images are covered by a "gray veil." This is attributed to the topical dependency of the speed of sound in the tissue, particularly in the subcutaneous fatty tissue which causes refractive effects Specifically in the field of high-quality B-scanners having extremely good resolution, which can practically be obtained only given employment of large apertures, it would be of significance if the percentage of patients that can be scanned with high image quality could be successfully increased. A method and a means would thus be desirable which reduce or largely eliminate the influence of, in particular, the inhomogeneities of the examined patient close to the skin in a medical ultrasound imaging apparatus given B-image acquisition. The functional principle must be capable of being applied without serious disadvantages for patient and examining personnel. It would be acceptable if the image were offered not in real time, but only as a still picture, or if a real time image were only supplied after a waiting time and restricted to one application location.

A method and imaging portrail system for examining soft tissue are disclosed by PCT publications WO No. 84/01433 (U.S. Pat. No. 4,484,477), WO No. 84/01434 (U.S. Pat. No. 4,471,785) and WO No. 84/01435. In accord therewith, disturbances in the image quality are reduced by correcting the delay times and amplitude occupancy of the active aperture of the ultrasound array. The correction is preferably carried out on the basis of a cross-correlation of signals of the elemental or primary transducer elements of the array, with more details regarding the precise procedure not being provided in the above documents. Value is attached to high processing speed, requiring special calculating circuits and thus an extremely high outlay. A cost-beneficial embodiment would be desirable.

SUMMARY OF THE INVENTION

An object of the present invention is to provide a method and an apparatus with which the image quality in the medical examination of patients can be enhanced in a cost-beneficial way in an ultrasound imaging apparatus using an ultrasound array wherein the influence of local inhomogeneities particularly in the subcutaneous fatty tissue of the patient examined, on the quality of the B-image is largely reduced.

As used herein the terms "local inhomogeneities" and "image-disturbing inhomogeneities" and "acoustic inhomogeneities" are inhomogeneities in the speed of sound in the patient.

The above object is achieved in accordance with the principles of the present invention in a method and apparatus based on the consideration that a measured value must first (i.e. in advance) be defined which in the examination of a patient, describes the nature of the acousto-physical inhomogeneities of the tissue situated in front of the ultrasound array. The topical curve of this measured value can then be taken into consideration in the actual (later) examination of the patient, in the form of correction values.

The above object is achieved in a method including the following steps:

(a) a sectional plane of the examination subject is first scanned in an adaptation phase with focused ultrasound transmission rays and unwanted effects caused by the inhomogenities are measured from the echo signals reflected by the examination subject;

(b) correction values for the delay times of the signals of the elemental or primary transducers of the ultrasound array in comparison to the standard focusing are derived from the measured values in this adaptation phase; and (c) the delay times of the active aperture of the ultrasound array are varied dependent on the correction values in the following B-image representation phase for the overall real time examination duration of this sectional plane in the emission and/or in the reception, whereby the unwanted effects are compensated.

An apparatus for the implementation of the method of the invention includes a correlator with which echo signals in the adaptation phase are correlated with one another via a prescribed correlation function.

The method and apparatus of the invention are based on a principle which could be referred to as the "principle of the adaptive antenna" or the "principle of the adaptive aperture modification".

Disclosed herein, thus, are a method and an apparatus by means of which the unwanted effects in the subcutaneous fatty tissue in the sectional plane of interest are measured once in the adaptation phase, and these unwanted effects are then compensated in the B-representation phase in every scan in the sense of an "adaptive antenna". The measurement of the unwanted effects which is executed first ensues only on the basis of the echo signals reflected from the body of the patient. No unrealistic conditions are made of these echo signals for the processing. The measurement is preferably based on the cross-correlation of the echo signals of neighboring elemental or primary transducers of the ultrasound array. For example, variations in the speed of sound in the examination path of the patient lying immediately in front of the ultrasound array are acquired from the shift of the maximum of the correlation function in comparison to the anticipated value for the homogeneous case. The correction values for the focusing during transmission and/or reception in the following B-image representation phase are derived from the measured values acquired in this manner.

A certain waiting time, which is caused by the identification of the correction values in the respective adaptation phase, is accepted in the examination of two different sectional planes.

Signal averaging means are preferably provided for protecting the measurement against artifacts.

The apparatus for generating an "adaptive antenna" in an ultrasound B-scanner may operate as follows. The unit has a scan button or key with which the automatic adaptation is initiated in every new scan position as long as the scan key or button is pressed. All the more complete scan runs are carried out for data protection in the adaptation phase the longer the scan key or button is pressed. For especially good adaptation, the operator tilts the ultrasound array slightly during the adaptation phase. The shortest possible time for the adaptation amounts to about 120 ms. In the examination phase after the adaptation, a fast scan can be executed in corrected form as long as the section plane is not too greatly modified so that noticeably different paths in the subcutaneous fatty tissue must be traversed. The "principle of the adaptive antenna" is thus also fundamentally suited for the portrayal of the heart. The tilting of the scan plane in the adaptation phase, however, is superfluous in this application due to the self-movement of the heart.

An improvement of the adaptation is achieved by applying an iteration method. In this embodiment the correction values acquired in a preceding (for example, first) adaptation phase are also employed as correction values for the following transmission case which initiates the next (for example, second) adaptation phase. An improved transmission focus is thus formed.

DESCRIPTION OF THE DRAWINGS

Exemplary embodiments of the invention shall be set forth in greater detail below with reference to the drawings. Shown are:

FIG. 10: equations related to "aligning" and to formation of the average values;

DESCRIPTION OF THE PREFERRED EMBODIMENTS

On the basis of published investigations, the ideas regarding the cause of the aforementioned effect of loss of image quality in the tissue which are currently held are as follows. Mainly, the topical dependency of the phase velocity (less the attenuation inhomogeneity) present in the body is caused by refraction of three disturbing effects:

(a) acoustic beam swivel, (b) acoustic beam spread, and (c) loss of symmetry of the acoustic beam profile.

The above sequence also reflects the ranking of the significance of the effects. As a consequence of the extremely low sound velocity of fatty tissue in comparison to organ parenchyma and muscle, the principal cause of the loss of image quality is suspected to lie in the inhomogeneity of the subcutaneous fatty tissue or "belly fat". By contrast, the liver is relatively homogeneous in its distribution of velocity.

Figure 1:
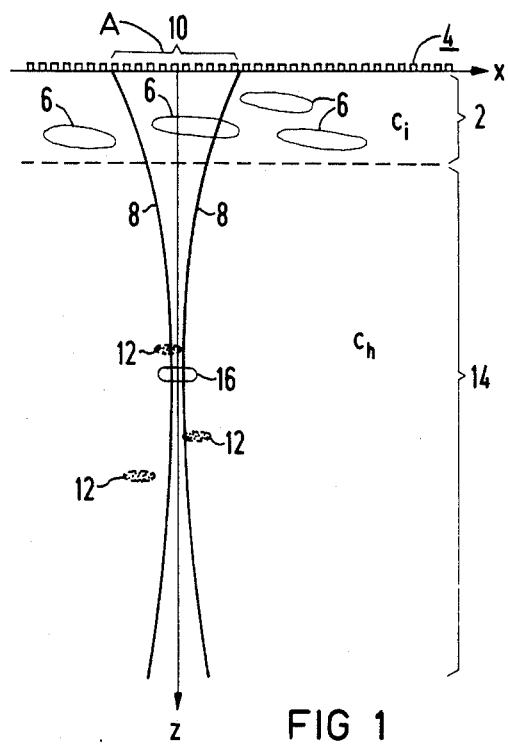
FIG. 1: a model of the ultrasound propagation in an examination subject with cloud-like reflectors.

So as not to unnecessarily complicate the object of compensating the afore-mentioned unwanted effects, the case of a disturbing layer 2 which is close to the transducer and is inhomogeneous with respect to the speed of sound shall be considered first. This situation is shown in FIG. 1. The disturbing layer 2 in the examination thus lies immediately in front of a linear ultrasound array 4 comprising, for example, 128 ultrasound transducer elements. The scan direction is referenced x and the B-scan line (central ray) is referenced z. The disturbing layer 2 (speed of sound $c_i$) contains a plurality of fatty inclusions 6. Also shown therein are the acoustic beam edges 8 (for example, $-6$ dB values) of the ultrasound beam emitted by the active aperture 20 as well as statistically distributed diffusing members or "point clouds" 12 as echoing diffusing centers in the following homogeneous medium 14 (speed of sound $c_h$). The point clouds 12 correspond to the currently held model for body-internal reflectors and contain a larger number (for example, 30 through 100) of punctiform diffusing particles in the volume of a resolution cell 16 of a standard B-scanner. Typically, this cell 16 is an ellipsoid having the dimensions $z=0.7$ mm in longitudinal direction, $x=3$ mm in transverse direction, and $y=5$ mm in slice direction for the $-6$ dB contours.

Figure 2:
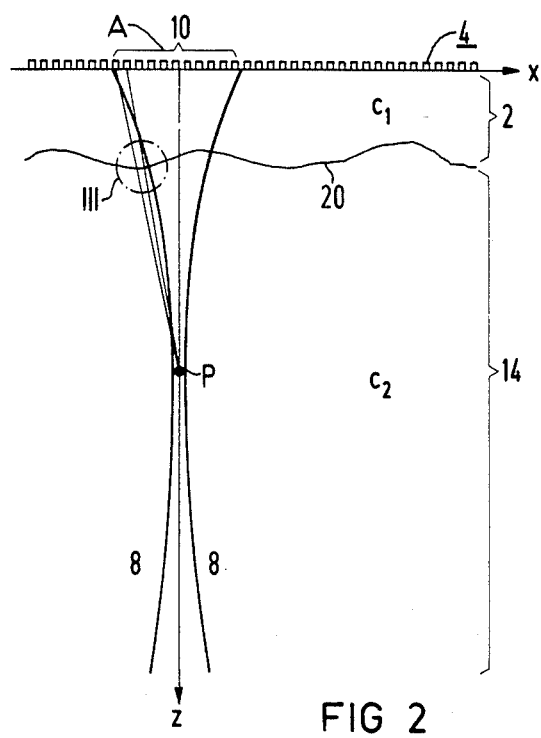
FIG. 2: a simplified model of the ultrasound propagation in an examination subject having point reflector.

In order to make the model for the initial considerations more easily able to be analyzed, the inhomogeneous disturbing layer 2 in FIG. 2 is shown by a plate of non-uniform thickness and having a speed of sound cl ($\neq c_2$) which differs from the medium 14 lying therebelow but which is uniform (topically invariable). Instead of a point cloud 12, further, only one echoing subject point P lying on the central beam z is initially assumed. In contrast to the known literature, it is not assumed that one or two point reflectors projecting in terms of amplitude are present in the subject plane. Such a "standard reflector" is not present in the human body. Consideration of a single point P only has didactic reasons here.

Figure 11A:
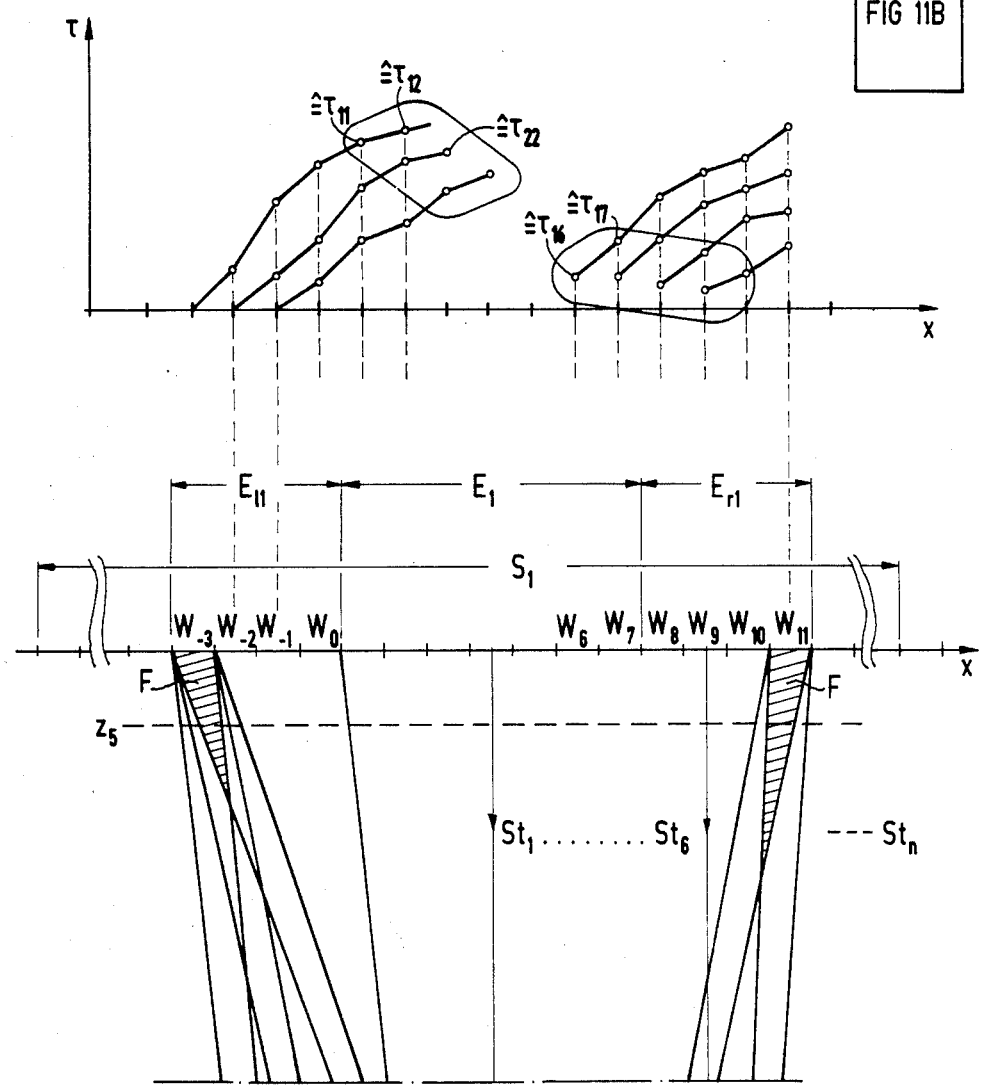
FIG. 11: the conditions given the addition of the boundary regions of the active reception aperture.
Figure 11B:
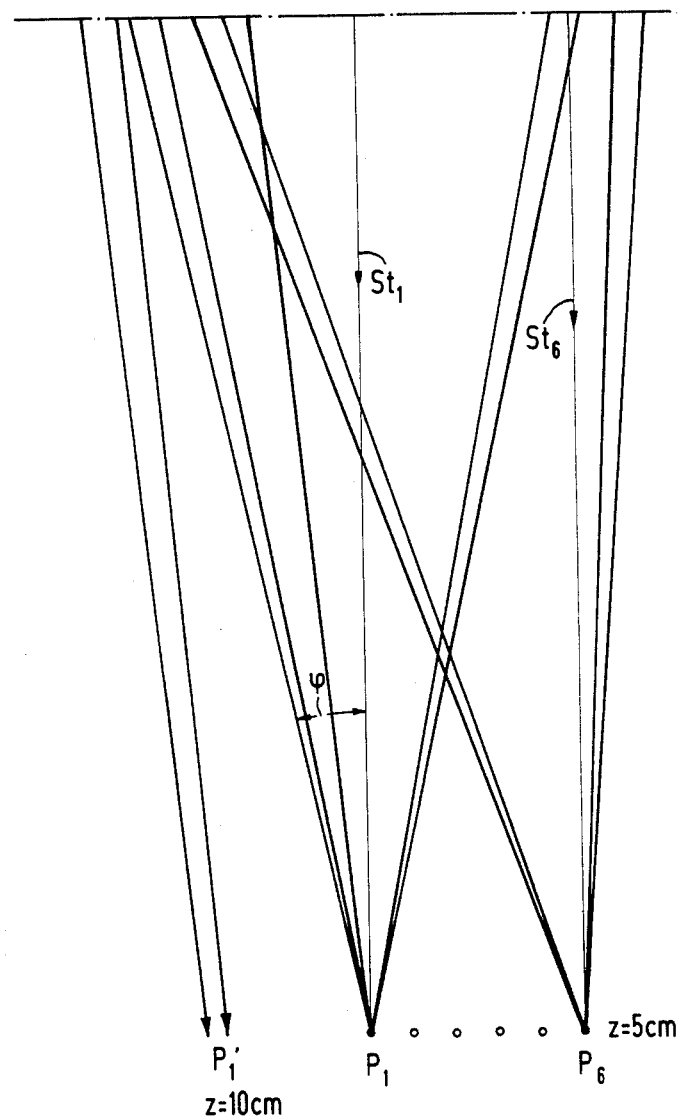

Likewise for didactic reasons, the refraction occurring at the boundary layer 20 between the two media 2 and 14 having different speeds of sound c1 and c2 will be initially left out of consideration until the discussion below relating to FIG. 11. In FIG. 2, the active aperture 10 emits focused ultrasound pulses, which run in the indicated, lateral boundaries 8 of the acoustic beam, into the examination media 2 and 14 and "illuminating" the punctiform deflector or diffusion member P. The travel paths on which the wave diffused by the subject point P reach the first two elemental primary transducers of the active reception aperture 10 on the transmission or reception array 4 are indicated in FIG. 2.

Figure 3:
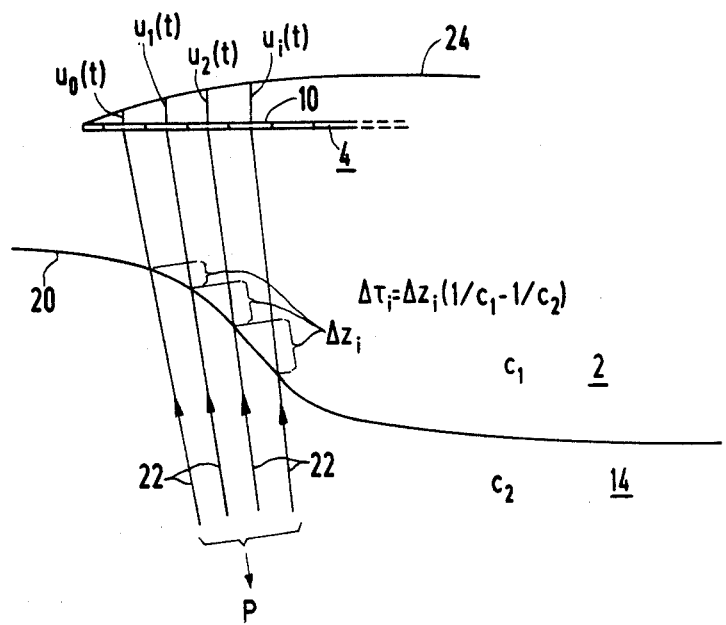
FIG. 3: an enlarged portion of FIG. 2.
Figure 4:
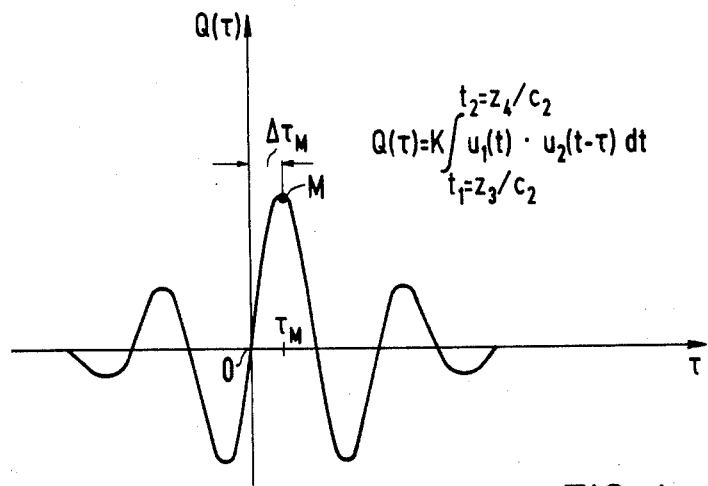
FIG. 4: a diagram for measuring the values $\Delta \tau_M$ from the cross-correlation of the reception signals by searching the maximum M.

The excerpt III comprising the passage of these reception paths 22 through the boundary layer 20 between the media 14 and 2 is shown enlarged in FIG. 3. One can see that transit time difference $\Delta \tau_i$ in comparison to a standardized-focused reception (on circular segment 24 around point P) correspond to the travel path differences $\Delta Z_i$. The circular segment 24 thereby corresponds to a spherical transducer cap focused by curvature (electrical delay). The time differences $\Delta \tau_i$ lead to a partly destructive interference of the echo or reception signals of the individual transducers of the array 4 in the known sum formation (also carried out here). Disturbing artifacts in the imaging therefore arise. In other words, the ultrasound B-imaging apparatus is set such that the individual echo signals $u_i(t)$ would add up without destructive interferences if the time differences $\Delta \tau_i$ were not present. According to FIG. 4, the time differences $\Delta \tau_i$ can be identified from the cross-correlation function $Q(\tau)$ of the echo signals $u_i(t)$ "received focused" of immediately neighboring elemental or primary transducers. Deviating therefrom, it is also possible to form respective groups of neighboring elemental or primary transducers, for example by direct parallel connection or by combining delayed echo signals, and to correlate the signals of two respectively neighboring groups. What is to be understood by the term "signals received focused" are the individual time signals $u_i(t)$ which are picked up by the elemental or primary transducers of the array and—given the assumption of a topically invariant speed of sound c2 in the entire examination space—which have been delayed such that, after electrical sum formation, this is equivalent to reception on, for example, a cylindrically or spherically curved transducer surface 24. The cylinder or sphere center lies at the location of P. Without velocity deviation, i.e. given homogeneous distribution of speed of sound, the (positive) maximum M of the correlation function $Q(\tau)$ lies at the time shift $\Delta \tau_M = 0$ because, theoretically, identical signal shapes are received by both transducers. The position $\tau_M$ of this maximum M (not of the minimums) on the horizontal axis $\tau$ is therefore a measure for $\Delta \tau$. The integral expression for the correlation function $Q(\tau)$ is likewise indicated in FIG. 4. The factors $u_1(t)$ and $u_2(t)$ are the echo signals of two neighboring elemental or primary transducers received focused and $\tau$ is the shift parameter. The function $Q(\tau)$ corresponds to the "cross-power" given varying, mutual shift $\tau$ of the two signals $u_1$ and $u_2$. The integration limits $t_1$ and $t_2$ derive from the depth region limits z3 and z4 and from the speed of sound c2 in the medium 14. The selection of these limits $t_1$ and $t_2$ shall be described below with reference to FIG. 6. The factor K can remain undefined because only the position of the maximum M, not its absolute height, is to be identified. FIG. 4 shows a typical curve $Q(\tau)$. The point M thus corresponds to the maximum of the cross-power. In order to identify M, and thus $\tau_M$, it is necessary to vary $\tau$ in the integral expression $Q(\tau)$ until the maximum of the cross-power is present.

Figure 5:
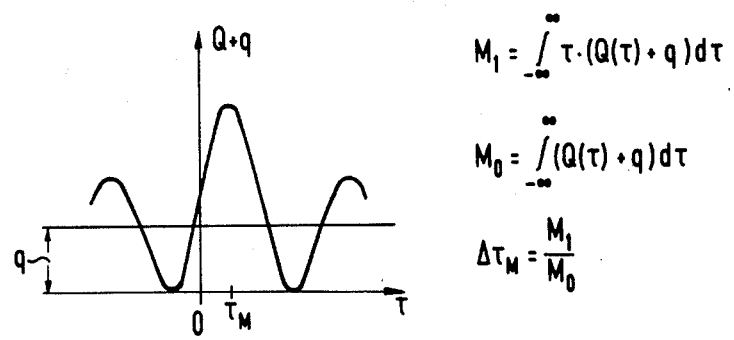
FIG. 5: a further diagram for measuring the values $\Delta \tau_M$ from the cross-correlation of the reception signals by forming moments.

Instead of the position of the maximum M which, for example, can also be found from the identification of the zero-axis crossing of the derivation of the function $Q(\tau)$, the position of the "center of gravity" line through the correlation function Q may be selected. This is derived from the quotient M1/M0 of the first and zero$^{th}$ moment M1 or M0 of the correlation curve $Q(\tau)$ shifted toward positive values by the amount q, according to the equations of FIG. 5. The constant q is selected such that negative function values of $(Q(\tau)+q)$ are reliably avoided, so that the denominator of M1/M0 cannot become zero. This calculation is carried out with a computer.

By adding all neighboring $\Delta \tau_M$ along the scan direction x (see FIG. 7) the transit-time distortion curve $\tau(x)$ effective across the aperture 10 can be acquired with supporting locations $x_1, x_2$... in the spacing of the array division of, for example, 1.5 mm. This procedure corresponds to a numerical integration, so that an integration constant still remains to be defined, which will be described below.

A point cloud 12 (see FIG. 1) will now be assumed instead of the point reflector T (see FIG. 2. One must then expect different signal shapes from neighboring elemental or primary transducers due to Bragg scatter. Transit time differences in the return paths of the echos which no longer overlay act in the same sense. Also, the point clouds 12 can only be "grazed" by the ultrasound beam 8—8, i.e., they do not have their center of gravity lying in the central beam z. The maximum M of the correlation function $Q(\tau)$ then no longer indicates the time shift $\Delta \tau_M$ undisturbed. Insofar as known, however, a clear correlation remains preserved given echos from the tissue. It is then assumed that, given averaging over many signals of many point clouds 12, the maximum shifts $\Delta \tau_M$ varying statistically on the basis of the Bragg scatter are emphasized and the shift produced by the inhomogeneous velocity distribution can thus still be measured with adequate precision. The reliability of the measured values is improved as more averaging is carried out. Simulation results confirm this assumption.

Figure 6A:
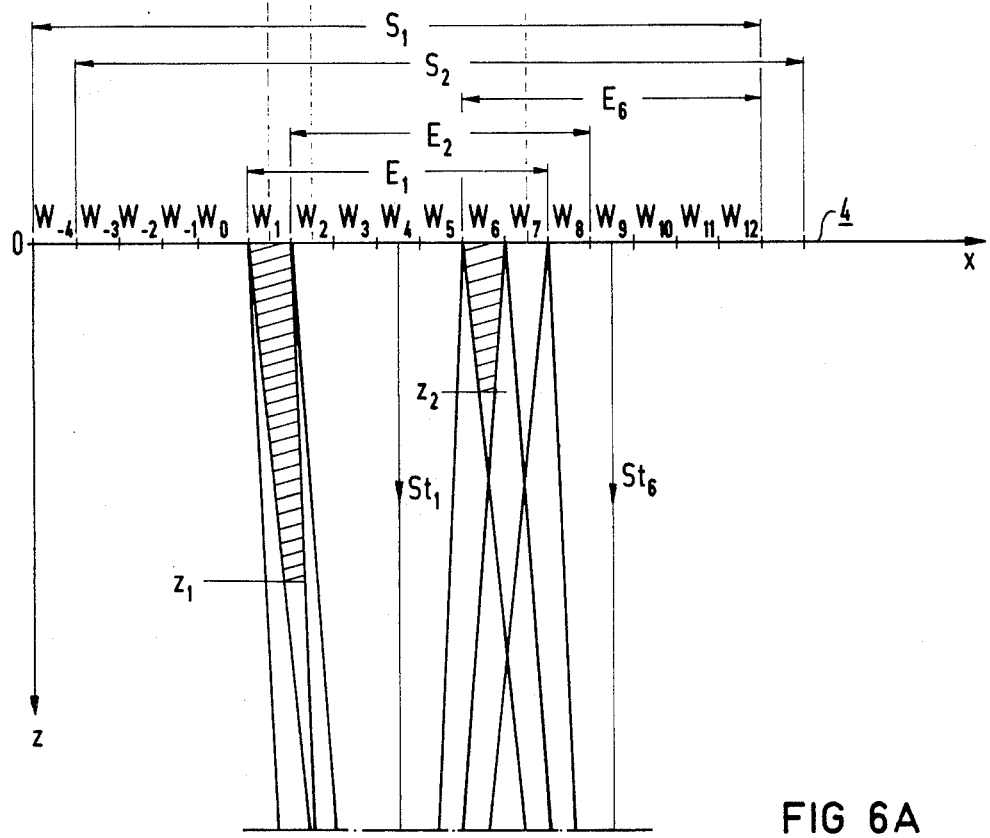
FIG. 6: the geometrical conditions in the parallel scan.
Figure 6B:
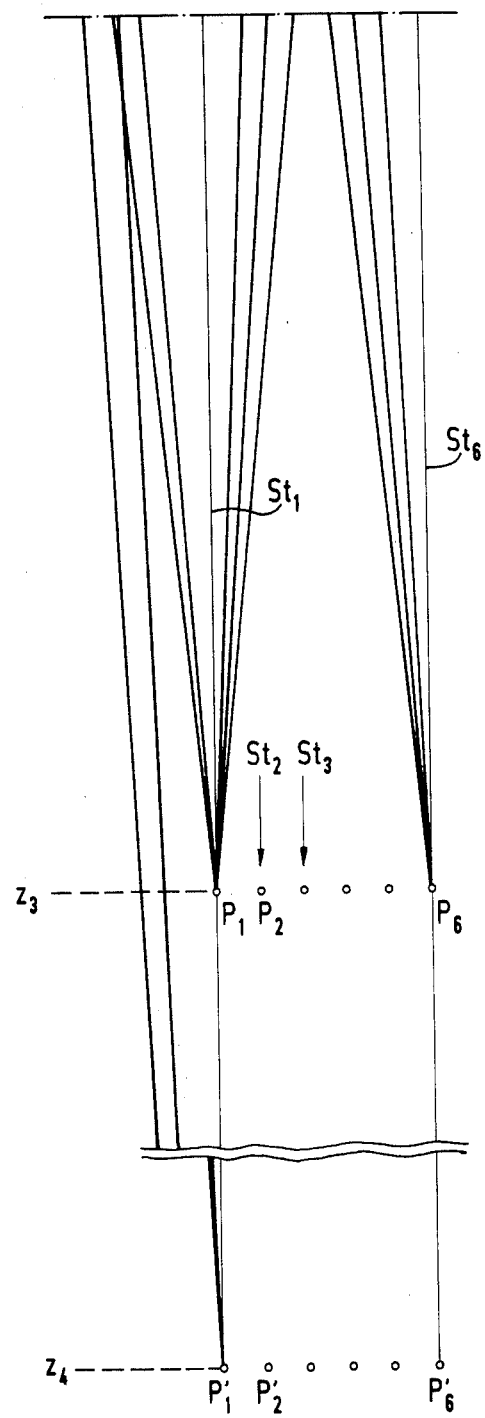

The following possibilities of averaging exist, and these methods can also be applied in combination:

In a first method, RF echo signals $u_1(t)$ of not only one resolution cell 16 but of an optimally great depth region of, for example, $z_3 = 5$ cm through $z_4 = 10$ cm are utilized for correlation (see FIG. 6). Approximately 10 through 30 greater echo complexes are to be anticipated in a human liver on this path $z_3$ through $z_4$. When observing such a depth region $z_3$ through $z_4$ it must be assured that the paths at the points $P_1, P_2, \ldots, P_6$ and $P'_1, P'_2, \ldots, P'_6$ at the depth region boundaries $z_3$ or $z_4$ do not proceed too differently in the region of the disturbing layer 2.

The path differences in the region of the disturbing layer 2 can be shown in the case of parallel scan with reference to FIG. 6. The effective transmission aperture of the elemental or primary transducers $W_p$ is consecutively referenced $S_1, S_2, \ldots$; their reception aperture is consecutively referenced $E_1, E_2, \ldots, E_6$. The "center of gravity" lines of the transmission beams are consecutively referenced $St_1, St_2, \ldots St_6$. A subject region having the limits $z_3$ and $z_4$ and the diffusion centers $P_1, P_2, \ldots, P_6$ and $P'_1, P'_2, \ldots P'_6$ is shown in FIG. 6 in roughly the scale 1:4. The elemental or primary transducers $W_p$ (for example, p=1 through 128) have, for example, a width of 1.5 mm corresponding to about 3 wavelengths at 3 MHz. The points $P_n$ lie at a depth $z_3 = 5$ cm and the points $P_n'$ lie in the depth $z_4 = 10$ cm. One can see the regions in which the spherical or cylindrical wave proceeds from the diffusion point $P_n$ to the elemental or primary transducers $W_p$. Given consideration of the points $P_1$ and $P_1'$, the return path to the transducer $W_1$ is dislocated by an acceptably small amount close to the transducer to the depth $z_1 = 1$ cm; about half an overlap at the lower edge given $z_1$ derives in the least favorable case. A coinciding travel path is thus assumed in the region $z=0$ through $z=z_1$. When the effective reception aperture $E$ is not broader than $E_1$ and the disturbing layer 2 is not thicker than 1 cm, thus, signals from the depth region $z_3 = 5$ cm through $z_4 = 10$ cm can be utilized for correlation with respect to the 7 elemental or primary transducers $W_1$ through $W_7$. (The case of wider reception apertures $E$ shall be discussed later.)

In a second averaging method, further noise suppression can be achieved if the measured values from a plurality of neighboring scan lines are averaged (see FIG. 6). The aforementioned path differences must also then be considered. It is also a prerequisite that the focusing design for the case of homogeneous velocity distribution functions well over the entire depth region. Under given conditions, this can be achieved with a dynamic focusing or with an axicon focusing (i.e. by geometrical or electronic simulation of an aperture shaped as a broadly inverted V).

The common return path from all points $P_1$ through $P_6$ and $P'_1$ through $P'_6$, which are placed in the signal capture region, remains as long as in the previous case immediately in front of the elemental or primary transducers $W_p$, up to the depth $z_2 = 0.5$ cm. Using a full-step method of the scanning (having a 1.5 mm step width in the example, corresponding to the width of a transducer element), the measured values of 6 neighboring scan lines can be averaged. Three or four lines are still admissible for a 1 cm disturbing layer 2. If the fluctuations of the measured values between the points $P_1$ through $P_6$ are great and if a greater averaging is therefore desired, the known half-step method (alternating activation of an uneven and of an even number of active elemental or primary transducers) could be applied and the number of admissible lines could thus be doubled. The usual thicknesses of the disturbing layers 2 of 1 through 2 cm can thus be acquired in practice with averaging over a not too small region.

A third averaging method for obtaining more mutually independent data undertakes measurement over a longer time span (for example, one heartbeat or one respiratory period) and averages these data. Differences of the echo signals which arise due to body-internal movement events are then acquired. The information otherwise occuring as speckle artifacts are then utilized.

Figure 12:
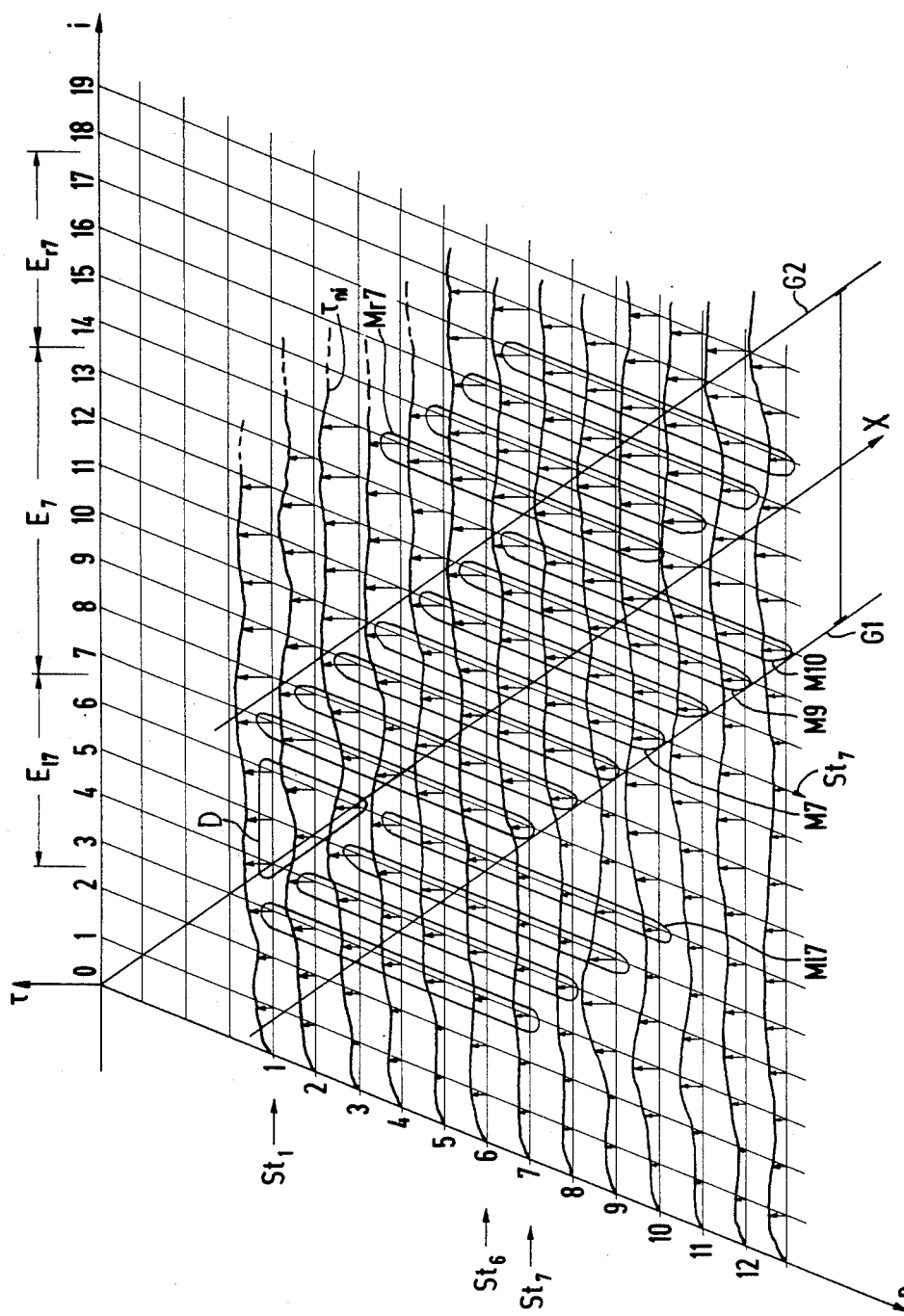
FIG. 12: a data field in the i-n plane for the measured values (parallel scan)

In this embodiment the measured curves of, for example, FIG. 12 are not produced only once, but repeatedly, as described later, and are averaged in a known way.

To augment the immediately preceding averaging method, an intentional, slight tilting of the array 4 can also be utilized to arrive at independent data. The expression "tilting of the array 4" means a small rotation of the sectional or scanning plane (for example, by 1° through 2°) around the longitudinal axis of the array (coupling surface) or scan axis x, so that the travel paths in the disturbing layer 2 differ only slightly from one another. It can be envisioned to undertake the tilting of the scan plane in the measurement automatically, i.e., electronically or mechanically. The electronic solution, however, presumes a multi-line array.

The correction extends more deeply into the tissue ($z_1$, $z_2$) as more averaging is undertaken according to the above four method embodiments, and or as the data capture field ($P_1, \ldots P_6$; $P'_1, \ldots P'_6$ according to FIG. 6) is made smaller.

Figure 7:
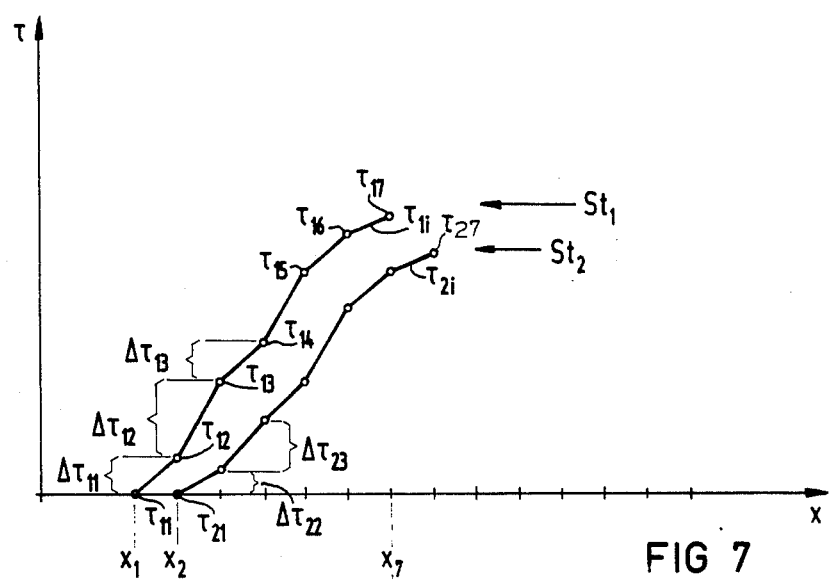
FIG. 7: the adding of the measured values in the parallel scans.

FIG. 7 shows the manner of adding of the measured values $\Delta\tau_i$ belonging to FIG. 6. The correlation of the signals of the elemental or primary transducers $W_1$ and $W_2$ yields the measured value $\Delta\tau_{11}$ after emission of the first transmission beam $St_1$, this measured value $\Delta\tau_{11}$ being arbitrarily entered proceeding from zero at the location $x_2$ of the transducer. $W_2$ and leading to the point $\tau_{12}$. The next measured value $\Delta\tau_{12}$ is derived from the reception signals of the transducers $W_2$ and $W_3$ and is entered at the location of $W_3$, beginning at the height of $\tau_{12}$. In the practical realization, it is added and stored in the computer. This leads to point $\tau_{13}$. One proceeds further in this manner to the curve point $\tau_{17}$. Subsequently, the transmission location ("center of gravity" line of the transmission beam $St$) is displaced one step (one element) toward the right, i.e. from $St_1$ to $St_2$, and measuring begins again. The measured values $\Delta\tau_{22}$, $\Delta\tau_{23} \ldots \Delta\tau_{28}$ are correspondingly added and yield a curve $\tau_{2i}$ laterally offset by one step comprising the same number of supporting locations $\tau_{21}$ through $\tau_{27}$. This procedure is continued over the entire scan length of the array 4. A plurality of curves $\tau_{1i}, \tau_{2i}, \tau_{3i} \ldots \tau_{pi}$ ($\tau_{ni}$) is thus obtained.

The adding harbors the risk that individual measuring errors will not only be locally expressed but will be "dragged" over the respective curve $\tau_{1i}, \tau_{2i}, \ldots$ It is therefore expedient to limit measured values which are greater than a physiologically occuring value for the increment $\Delta\tau$ per array division $W_i$ to the maximum value, or to remove them entirely under certain conditions.

As an example, FIG. 8 again shows the schematic course of the curve $\tau_{1i}(x)$. A linear regression line AG is placed through this curve. The only item of interest now for the further processing is the respective time interval $a_{1i}$ between the curve $\tau_{1i}(x)$ and the compensation straight-line AG. The individual time intervals $a_{1i}$ are stored and converted into correction values, as described below. A significant feature in this further-processing method is its simplicity; a correlation to the neighboring curves $\tau_{2i}, \tau_{3i} \ldots$ is not produced.

Another method can also be used instead of the method described immediately above. The values $\Delta\tau$ added according to FIG. 7 should initially contain only the averaging over echo signals from different depth position $z_3$ through $z_4$ of a scan line $St_1, St_2, \ldots$ An averaging over neighboring scan lines must still be done. (Further, the curves are still to be placed in relationship to one another.) This further averaging over neighboring scan lines can then be undertaken either before or after the adding of the $\Delta\tau$ values. The latter possibility shall be discussed here first because it is the more universal possibility.

Figure 9:
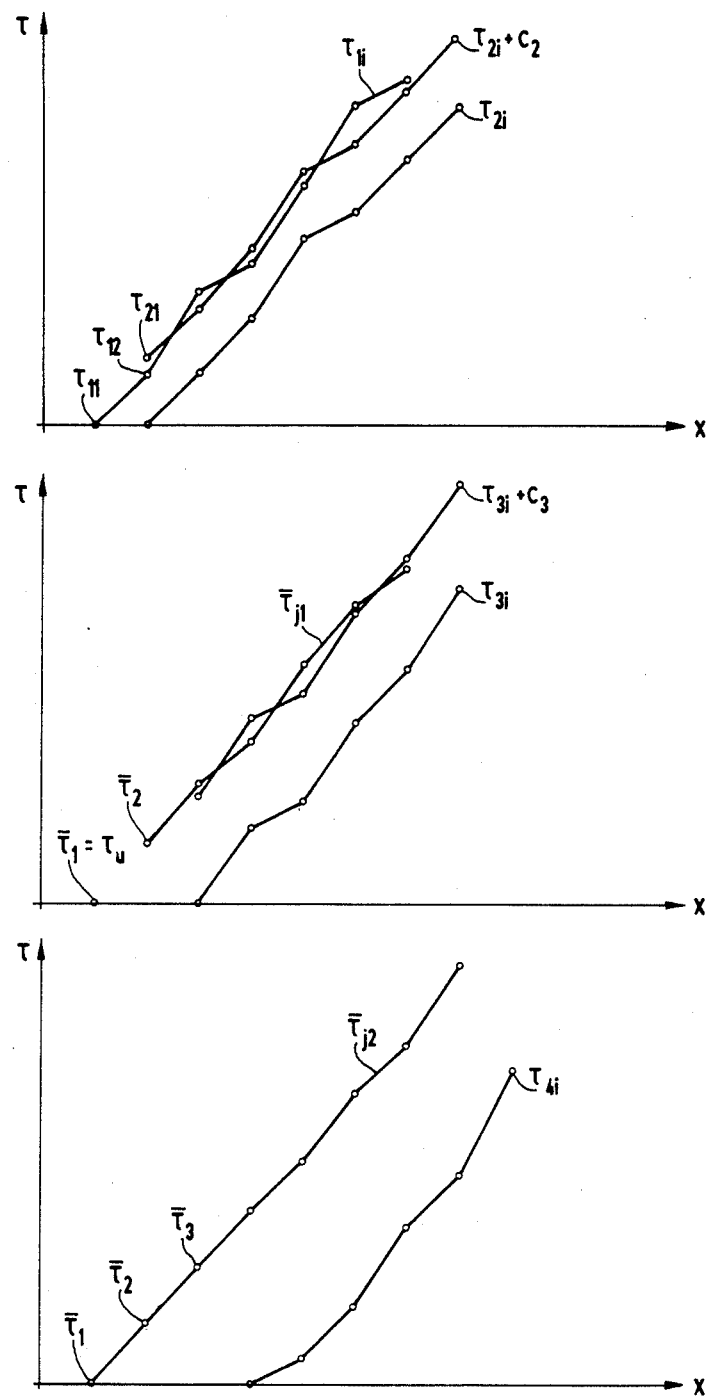
FIG. 9: a diagram for explaining an alternative further processing, referred to as "aligning" and of the formation of the average value.

The curves $\tau_{1i}, \tau_{2i}, \ldots$ (in general: $\tau_{ni}$) contain in part measured values over substantially identical travel paths in the subcutaneous fatty tissue, so that averaging can be carried out over values in more than one curve. FIG. 9 shows averaging of the measured values over a plurality of scan lines. The added, i.e. numerally integrated curves $\tau_{ni}$ are still arbitrarily shifted relative to one another because of the unknown integration multiplication constant (see, for example, constant K in FIG. 4). Before the formation of the average value, they must at least still be brought into relationship with one another. Knowledge of the absolute value of the integration constant is not necessary for the averaging.

One can proceed in the following way. As shown in FIG. 7, the curves $\tau_{ni}$ represent disturbed measured values for every elemental or primary transducer $W_i$. If the measured values were undisturbed, the curves $\tau_{ni}$ could be brought into coincidence by shifting in the $\tau$-direction (addition of different constants). The real measured curves are therefore initially overlaid according to the "method of the least squares error" or are brought into coincidence. This is referred to herein as "bringing into coincidence" or as "aligning". The graphic illustration of this method is shown in FIG. 9; the mathematical equations (1) through (6) for the "aligning" and for the formation of average values are shown in FIG. 10.

One begins with an arbitrary individual curve $\tau_{ni}$ in an arbitrary shift, for example with $\tau_{1i}$ in the illustrated position wherein $\tau_{11}=0$. The index n refers to the number of the transmission direction $St_n$. The neighboring curve $\tau_{2i}$ is shifted over the curve $\tau_{1i}$ by addition of a constant $C_2$. The value of the constant $C_2$ derives, according to equation (1), from the minimum Min of the sum of the quadratic differences. The first average value curve $\bar{\tau}_{j1}$ can be formed according to equation (2), cf. FIG. 9 center diagram, from the two curves $\tau_{1i}, \tau_{2i}$ which are now placed on top of one another ("aligned"). As a left side boundary value, this contains the second value $\bar{\tau}_2$ of the ultimately averaged result curve. The first value $\bar{\tau}_1$ is identical to the left-hand boundary value $\tau_{11}$ of the first, unaveraged measured curve $\tau_{1i}$. The value $\bar{\tau}_2$ is the average value of only two measured values. The value $\bar{\tau}_3$ (see the lower diagram in FIG. 9), correspondingly, is the average value of three measured values, etc. A maximum of seven values are averaged in the present example, so that fully averaged values are present beginning with $\bar{\tau}_7$ (not shown). One arrives at $\bar{\tau}_3$ by the "aligning" of $\tau_{3i}$ (middle diagram) with the first average value curve $\bar{\tau}_{j1}$ (middle diagram) in accord with equation (3) and averaging according to equation (4). The equations are written in FIG. 10 up to $\bar{\tau}_4$. The formation rule for the further curve points is thus clearly described. When a curve for all locations of the elemental or primary transducers $W_1, W_2 \ldots$ is present in this fashion, a correction of the focusing is undertaken, as discussed below.

Figure 8:
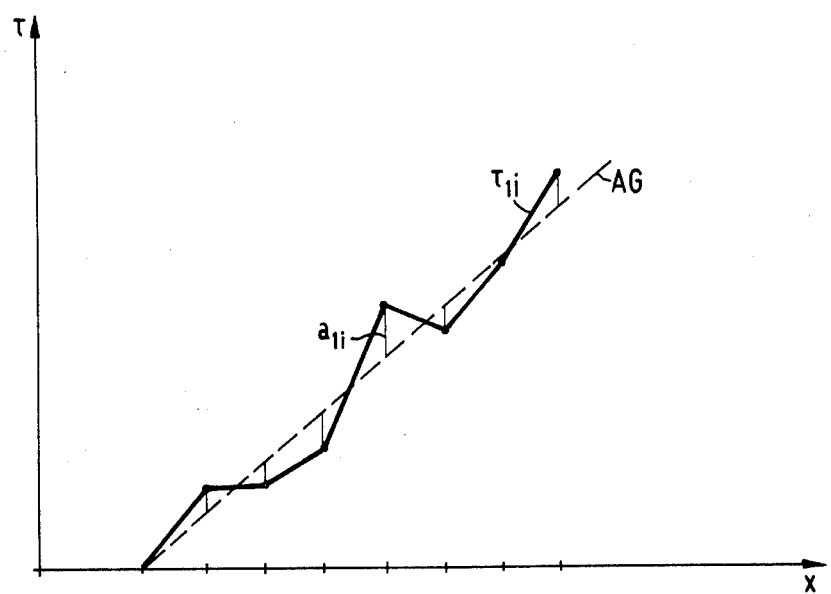
FIG. 8: a diagram for a simple further processing.

Instead of the methods respectively described with reference to FIG. 8 and to FIGS. 9 and 10, a high-pass filtering in the spatial region x (see FIG. 7) can also be executed in the further-processing. The filtered values of different curves which belong to the individual transmission locations $St_n$ are then subsequently averaged. The averaged values are stored and converted into correction values for the focusing in the reception and/or transmission case.

As initially stated the method disclosed herein should give relatively precise results given large apertures. In the discussion thus far, however, the correction possibility has been directed only to relatively small reception apertures of, in the example, seven elemental or primary transducers $W_1, \ldots W_7$ corresponding to 21 wavelengths or 10.5 mm. When larger apertures than $E_l$ (FIG. 6), i.e. apertures including $E_{ll}$ and $E_{rl}$ are considered, the travel paths to be measured as shown in FIG. 11, are no longer approximately perpendicular under the array, as in FIG. 7, but are slanted having an angle $\phi$ relative to the z-direction. In these regions, thus, one can no longer work with the previously identified values because they are valid only for the roughly perpendicular case.

One therefore proceeds such that the values $\tau_{ni}$ in the left and right edge regions $E_{ln}$ or $E_{rn}$ and, under given conditions, in further regions are incorporated in the way described above, including adding. This is shown in FIG. 11, top. In this manner, the measured values with respect to a transmission location $St_1, St_2, \ldots St_n$ are brought into coincidence ("aligned") for the entire reception aperture. The expectation of a steady curve course even in the transition region between the sub-apertures $E, E_r, E_l$, etc. is relied upon. These values for oblique sound incidence, of course, must be kept separate from the previous values and may only be averaged with one another, i.e. separately for left and right or, in general, averaged separately for every angle range $\phi$ relative to perpendicular sound incidence. Before or after their averaging, moreover, the measured value curves for every transmission location $St_1, \ldots St_n$ must be adapted ("aligned") to those already existing (for the inner aperture $E_l$) with respect to the integration constant. In the form of shaded areas F, FIG. 11, bottom, shows the maximum thicknesses $z_5$ of the disturbing layer permitted by the size of the selected field between $P_1 \ldots P_6$ and $P'_1 \ldots P'_6$, from which are used for averaging, which still allows usable measurements. The extreme values of the sound incidence from the points $P'_1$ and $P_6$ are thereby again entered and $z_5$ is selected in a depth which corresponds to a bisecting of the base of the triangle F.

The measured data acquisition leads to an entire data field which is three-dimensionally shown in FIG. 12. The summed times $\tau_{ni}$ may be seen as small arrows above the i-n plane. The index i indicates the place number of the elemental or primary transducer $W_1, W_2, \ldots$; n indicates the number of the transmission direction or of the transmission location ("center of gravity" line of the transmission field). The case of an aperture in the middle of a long, linear array is assumed (parallel scan). The reception aperture $E_{l7}, E_7, E_{r7}$ as well as the transmission location $St_7$ are specifically emphasized in FIG. 12. Edge effects due to the finite array length are not taken into consideration. The boundary lines G1 and G2 between which the indicated, horizontal curves are "aligned" to one another according to the methods, previously specified when scanning in scan direction X are entered in the plane, and those values that are averaged after the "aligning" are bounded by closed curves Mn, for example M7. This should remain unaltered given incorporation of the edge apertures as well. When one proceeds on the basis of the aforementioned expectation that the integrated curves $\tau_{ni}$ belonging to a transmission location $St_n$ must proceed steadily, then the edge regions are already "aligned" with the central reception region. For "aligning" with the curves of other transmission locations, it is expedient to average the curves in the position in which they came to lie due to the superimposition of the values for the center of the aperture ("aligning" in the perpendicular reception case). The values to be averaged are, again bounded by curves Men and Mrn, for example Ml7 and Mr7, for a position of the reception aperture. It is thereby insured that only values belonging to a fixed angular range $\phi$ of the deviation from the perpendicular sound incidences are averaged. The results can thus be employed independently of the scan location. If, for example, the region referenced D were also employed for averaging, this would be acceptable in the example for the scan location $St_1$ but not, for example $St_6$.

Figure 13:
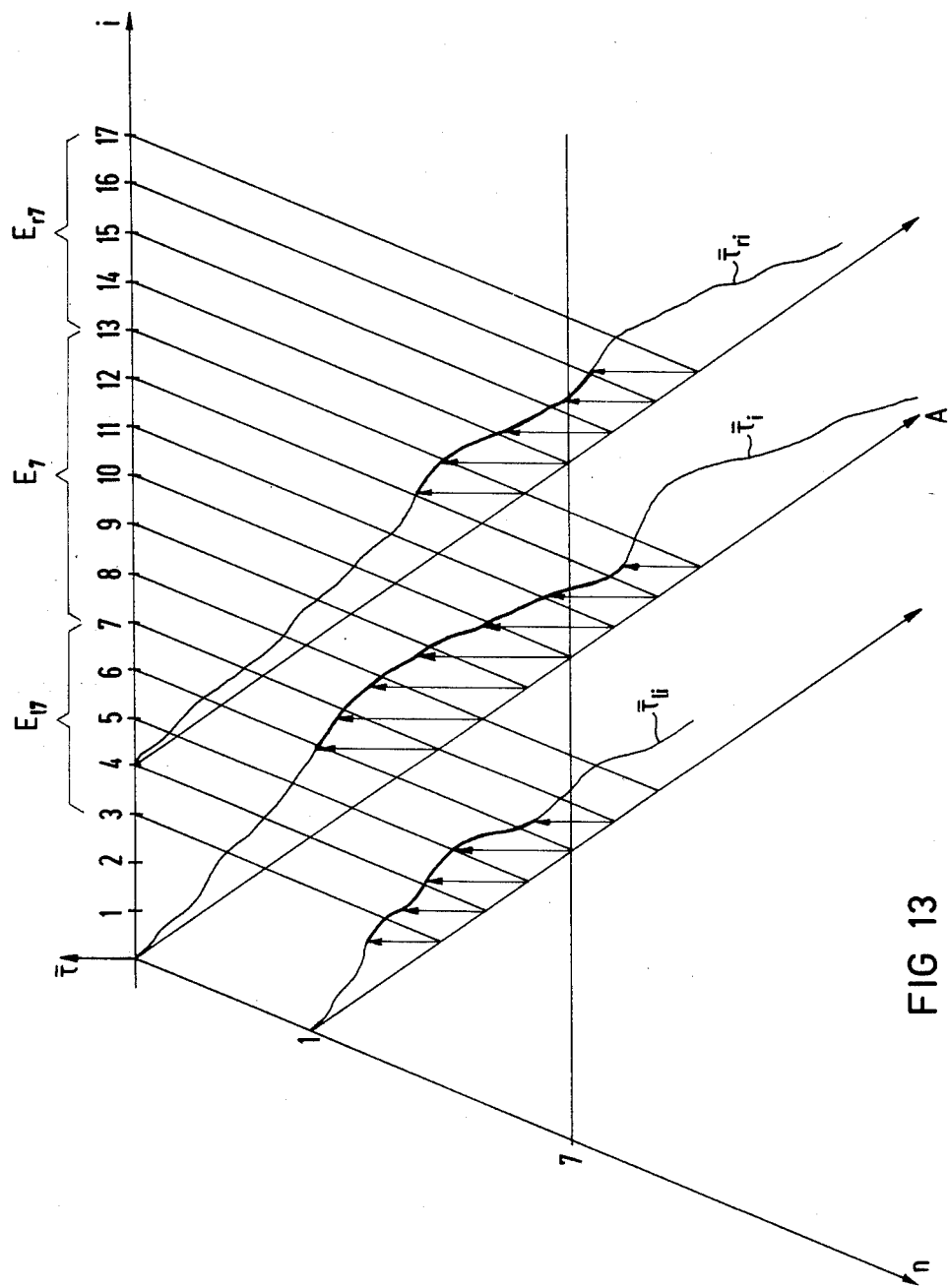
FIG. 13: a data field in the i-n plane for the averaged measured values (parallel scan)

The result of the averaging is compiled in the i-n-$\tau$ diagram in FIG. 13. Given a central reception region $E_7$ of the aperture and left and right edge regions $E_{l7}$ and $E_{r7}$, one obtains three averaging curves $\bar{\tau}_i$, $\bar{\tau}_{li}$ and $\bar{\tau}_{ri}$. The curve parts drawn with heavy lines apply to the illustrated position of the reception apertures $E_{l7}$, $E_7$, $E_{r7}$. The curves proceed step-by-step diagonally toward the right front with the scan A. The left and right curve ends are less greatly averaged due to the finite array length and are thus less reliable than the (longer) middle parts. In the imaging, however, this only has an influence on the edges of the image. As a result of the "aligning" only from the middle region, the edge region curves are likewise less reliable than the curves for the aperture middle.

Curves relating to the transit-time distortion in the transducer-proximate disturbing layer are thus present, and are employed for the correction of the focusing error. Only an integration constant shared by all curves is unknown. The constant corresponds to a plane-parallel disturbing layer whose speed of sound $c_1$ is unknown. Since such effects lead only to slight disturbing errors of the image geometry in practice, a further measuring step is superfluous. For better understanding, a common constant G can be added to all curves which is sure to avoid the negative curve values at any location whatsoever.

If one again initially considers only the central reception region $E_7$, it is possible as an alternative to the method discussed in connection with FIG. 11 to average the $\Delta \tau_{ni}$ curves or, equivalently, the differentiated curves of FIG. 7 in order to simplify the calculating rule, and to undertake the integration only subsequent to the averaging. Although the integration constants $C_2$, $C_3$, $C_4$ of FIG. 10 are then not acquired, no important information is lost because these constants are not further employed.

When, however, the reception edges $E_r$, $E_l$, etc., are also to be measured, the integration constant $C_2$, $C_3$, $C_4$ ... are nonetheless important because the integrated curves $\tau_{ni}$ must be "aligned" relative to one another. Non-physiological discontinuities can occur when—dependent on the beginning of integration—arbitrary integration constants can be selected. There is no boundary condition for the transition between the regions for the curves which are already averaged because a new category of measured value curves for oblique sound incidence is involved. There is only the afore-mentioned steadiness expectation for the curves which are not yet averaged but are already integrated. This simplified calculating possibility, thus, can only be utilized to a very restricted degree.

Instead of the correlation of the signals of neighboring elemental or primary transducers $W_1$, $W_2$, ..., the correlation of the signals of the elemental or primary transducers can also be formed with the sum signal of the focused reception aperture for measuring the transit-time distortion curve. This, however, results n measured values that are not as good because the relationship of the reception signals is not as great as for the signals of neighboring elemental or primary transducers.

Figure 21:
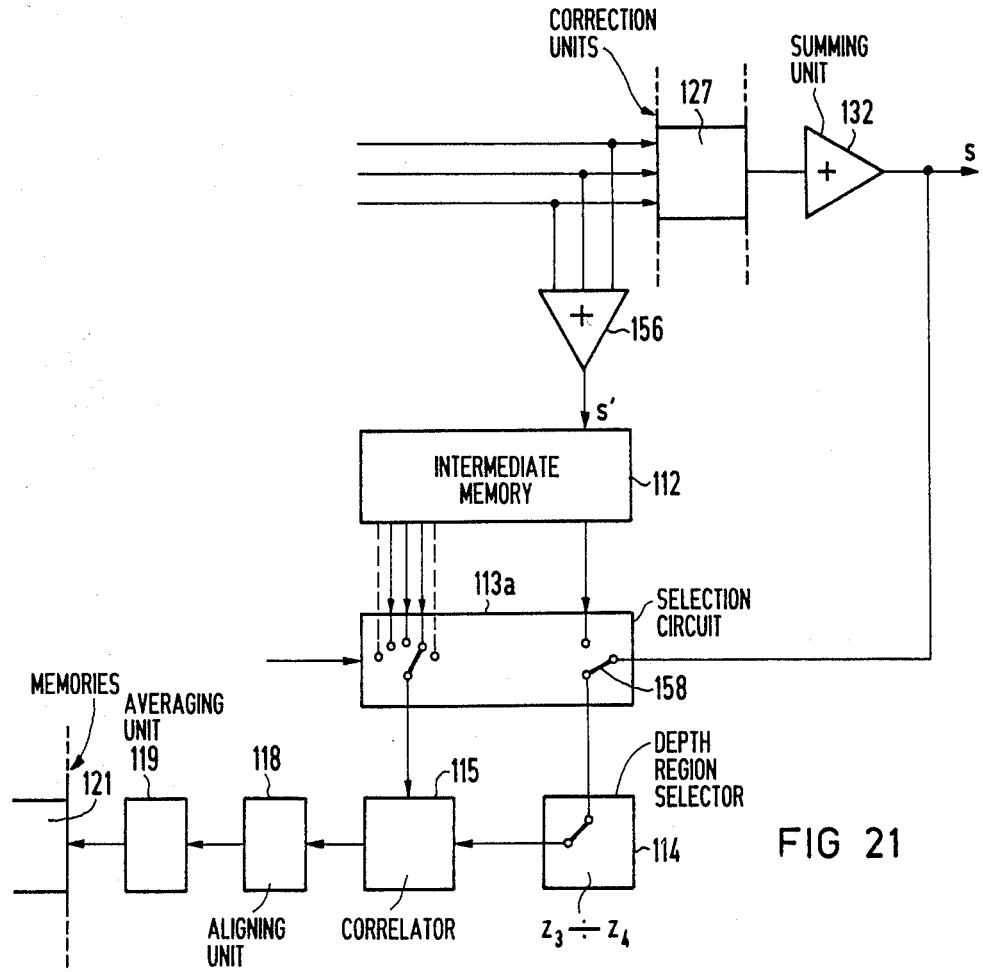
FIG. 21: a portion of a block circuit diagram upon application of a correlation with the sum signal.

Given this method, an equivalency to the integrated curves of, for example FIG. 12, is directly obtained by measurement. The further signal processing is executed as specified later. A technical application is shown in FIG. 21.

Figure 14:
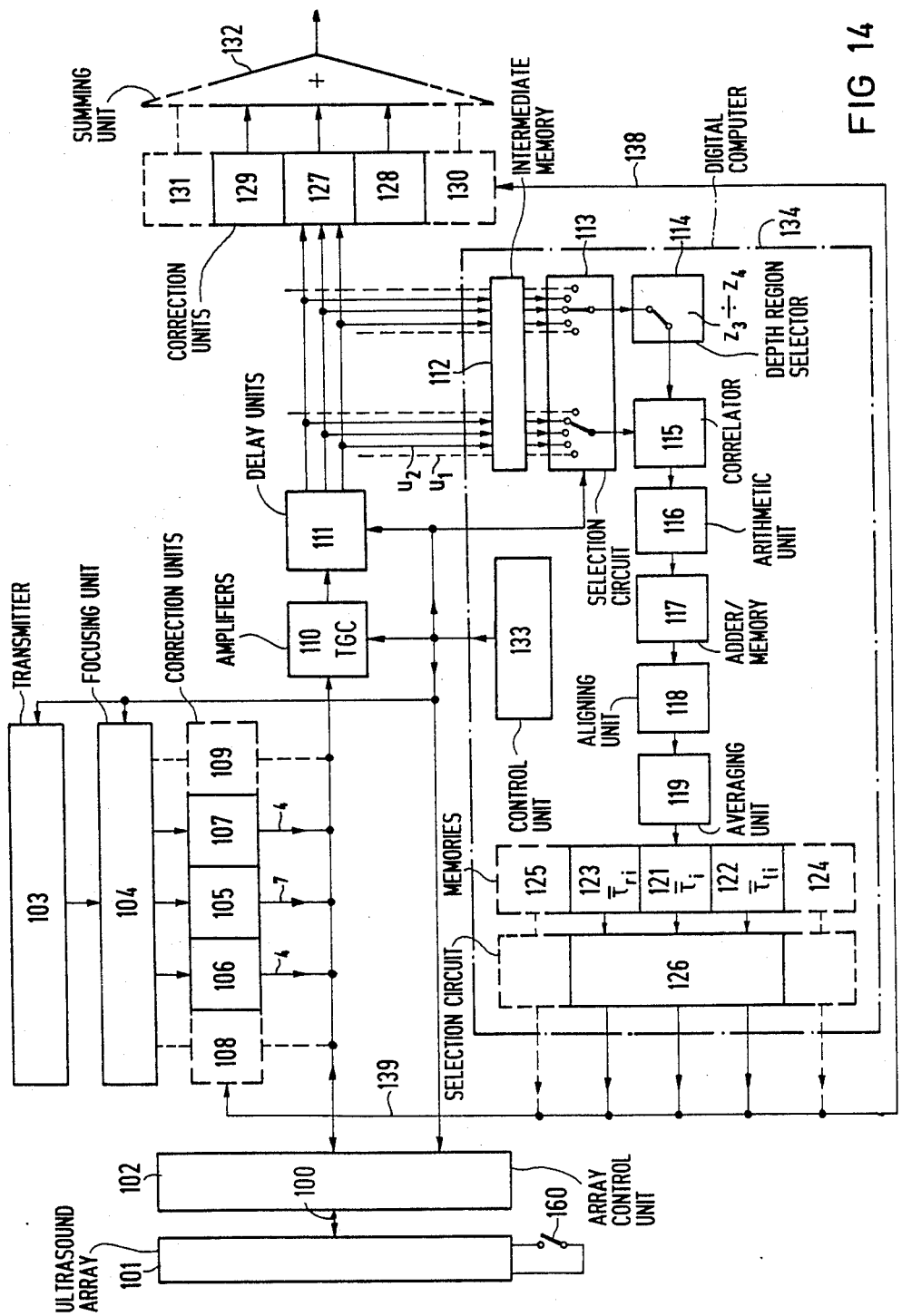
FIG. 14: a block circuit diagram of an ultrasound B-imaging apparatus having an adaptive antenna.

The input stage of an ultrasound imaging apparatus, specifically of a B-scanner, which undertakes the described measuring method for the velocity variations in the belly fat or subcutaneous fatty tissue for compensation of the focusing errors thereby produced is shown in FIG. 14.

This input stage includes a linear ultrasound array 101 comprising, for example, 100 transducer elements $W_1$, $W_2$ ..., and a beam control unit 102 for scan stepping or for pivoting the emitted ultrasound beam. The array 101 is operated by the unit 102 in the sense of an electronic parallel or sector scan. A transmitter 103 and a focusing means 104 operate in accord with conventional technology as though the transmission medium were homogeneous. The correction units 105 through 109 between the transmitter 103 and the focussing means 104 are initially ineffective.

In the final stage of the adaption and duration, all transducer elements $W_1$, $W_2$, ... are preferably utilized for the active reception aperture A and transmission aperture A. The reception signals of the active area of the array 101 are amplified by TGC amplifiers 110 and are delayed in reception focused delay units 111 in accord with the known prior art, such that a well-focused reception signal would result following a summing element 132 and given a homogeneous transmission medium. The reception signals of the elemental transducers $W_1$, $W_2$, ... can, under given conditions, be intermediately stored in a memory 112. The lowest possible number of transmission bursts can be used and, given a correspondingly fast signal processing, the adaptation process sequence has the shortest possible time. Without this intermediate memory 112, re-transmission would have to be undertaken with every signal pair. The memory 112 is arranged following the delay units 111. As a result, the anticipated values for the position of the maximum M of the correlation function $Q(\tau)$ according to FIG. 4 become zero for the homogeneous case. Alternatively, the memory 112 can receive the reception signals between the TGC amplifiers 110 and the delay units 111. The anticipated values are then unequal to zero.

Two respective signals, for example $u_1$ and $u_2$, of neighboring elemental transducers are selected preceding a summing unit 132 in a measured value selection circuit 113. These signals are forwarded to a correlator 115 for correlation processing. The selection circuit 113 cyclically steps to two new signals, so that the entire array aperture is scanned in combination with the control unit 102. A depth region selector 114 selects the depth region $z_3$ through $z_4$ from which the echo signals are to be correlated. In an arithmetic unit 116, the distance $\Delta \tau_M$ of the maximum M of the correlation function from the origin is identified for every signal pair (for example, u1, u2 or u2, u3), and is added to $\tau_{ni}$ in a following adder and memory 117, so that the curves $\tau_{ni}$ arise in the form of tables (see FIG. 12) of the stored supporting location values. In an aligning unit 118, the constants $C_2, C_3, C_4, \ldots$ are calculated according to the equations of FIG. 10, i.e. a central "aligning" is carried out. An averaging unit 119 undertakes the following formation of the average value.

The functions $\tau_i$ of FIG. 13 are deposited in a following memory 121. The values $\tau_{ri}$ are deposited in the memory 122; and the values $\tau_{li}$ are deposited in a memory block 123. The storing of further data is indicated with two broken-line memories 124 and 125, these further data arising when even more edge regions (not shown here) of the reception aperture $E_{l7}$, $E_7$, $E_{r7}$ are also measured. A selection circuit 126 undertakes the selection of the time-delay values which are required for the correction (described below in connection with FIG. 15) of the even-numbered active transducers. This corresponds to the curve parts in FIG. 13 drawn with thick lines.

Correction units 127 through 131 are connected between the delay units 111 and the summing unit 132. A control unit 133 is provided for controlling the individual function executions. The output of the summing unit 132 leads in a known way to a demodulator for the image signal. The actual correction of the time-delay values is carried out in the correction units 127 through 131 in the reception case and is carried out in the correction units 105 through 109 in the transmission case. These are controlled by the selection circuit 126 via lines 138 and 139.

The components 112 through 126 and 133 can be interpreted as parts of a digital computer 134 which undertakes the overall control and undertakes the above-presented type of processing the measured values up to the formation of the curve family of FIG. 13. The analog-to-digital converters which are then required are not shown here. It is also inconsequential whether the especially fine sampling of the time signals required for the measurement of the small $\Delta \tau$ is directly supplied by the analog-to-digital converter or whether low-pass filtering is carried out in the computer 134 following minimal scanning according to the sampling theorem and over-sampling is subsequently carried out. The digital computer 134 can either be a universally programmable computer (being a cost-beneficial solution) or can be constructed of specific digital components (leading to faster data processing).

Instead of making the correlation calculation directly in the time domain in the correlator 115, a transformation to Fourier space, i.e. an identification of the complex cross-power spectrum, and a back-transformation into the time domain, is also possible based on current knowledge of system theory.

For reasons of processing speed or of costs, however, it can also be advantageous to undertake the correlation of the signals selected by the selection circuit 113 in the correlator 115 with specific components in analog fashion (i.e., not digitally). The interface to the computer 134 will then lie between the units 115 and 116. In this case as well, the correlator 115 runs through the parameter $\tau$ and it forms $Q(\tau)$ from $u_1$ and $u_2$. The maximum M is then derived, which is further-processed in the following unit 116 to form the measured value $\Delta\tau$ max.

Figure 15:
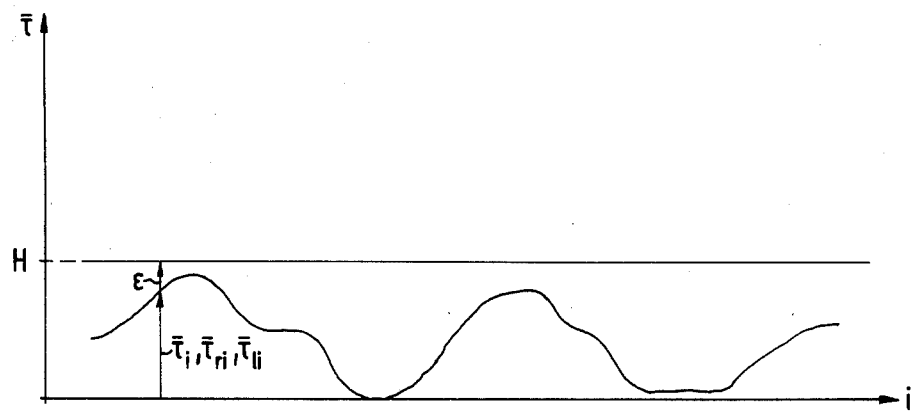
FIG. 15: a diagram for illustrating the correction of the transit-time distortion in the unwanted slice.

The correction with the units 105 through 109 and 127 through 131 fundamentally ensues in the manner shown in FIG. 15. The calculated curves $\bar{\tau}_i$, $\tau_{ri}$, $\bar{\tau}_{li}$ reproduce the transit time losses in the disturbing layer in comparison to an imaginary, plane-parallel, homogeneous layer. In the transmission and reception case, these transit times are augmented up to a constant value H which lies just high enough that no negative delay values arise, because these would not be realizable. The computational identification of these augmentations $\epsilon$ and the execution as auxiliary delay for the purpose of correction is carried out by the units 105 through 109 in the transmission case and by the units 127 through 131 in the reception case. In addition to the unit 111, thus, the units 105 through 109 and 127 through 131 contain electronic time-delay elements.

Figure 16:
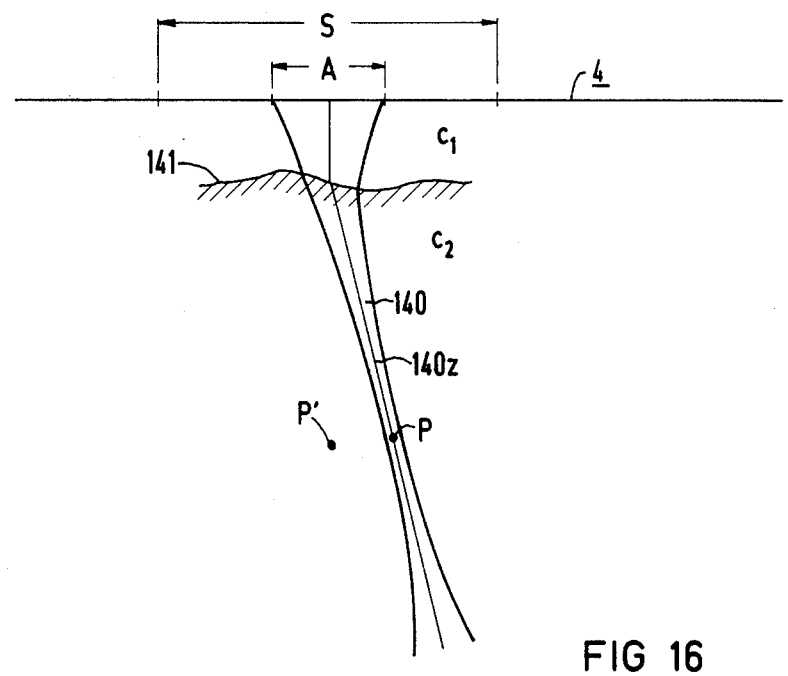
FIG. 16: an illustration of the effect of the size of the active aperture.

The time at which these correction units 105 through 109 and 127 through 131 take effect is derived with reference to FIG. 16. The transmission beam 140 of the transmission aperture S is shown broken away from a boundary layer 141 of the perpendicular emission from the array 4, this boundary layer 141 being smooth in the acoustic beam but proceeding obliquely relative to the array 4. Since the boundary layer 141 is smooth, the acoustic beam width remains uninfluenced. The reception sensitivity of the focused receiver (the same aperture A as in the transmission case is initially assumed) proceeds in the same boundaries. The signals from the centrally impinged point, i.e. from the point P lying on the central beam 140z come together equiphase as in the undisturbed case—after focusing delay. The refraction is not registered with the method specified above. Only variations which lead to a beam spread or which derive from a curved or wavy boundary layer 141 in the beam region 140 are identified. The situation would be different if the echos—as anticipated—came from the point P'. This can be approximately induced with a transmission aperture S which is far greater in comparison to the reception aperture A, because a continuously oblique boundary layer 141 is more improbable the greater the transmission aperture S.

The measurements are thus carried out with the greatest possible transmission aperture S even if, due to dynamic transmission focusing far more time is required than is actually allowed for a real time image. The test run must be carried out in the adaptation phase only once for an application location preceding the actual measurement (B-image examination phase; unless the array 4 is greatly tilted, so that the scan plane is greatly displaced). This time is thus not a disturbing factor.

A further improvement of the measuring precision can be recorded when an iterative procedure (iteration method) is selected. Following the first measurement in the described fashion, a correction is first undertaken only at the transmission signal; another adaptive measurement in the fashion set forth above is executed with this corrected transmission signal. The transmission lobe thereby already exists in improved form and the measurement is less disturbed by refraction effects. Under certain conditions, a plurality iteration steps can be selected.

A problem arises when the transmission aperture—as proposed—is as large as possible, and thus wider than the reception aperture under certain conditions, and when no correction values for the corresponding oblique travel paths are thus present. One solution is to select the reception aperture of the same width as the transmission aperture.

Figure 17:
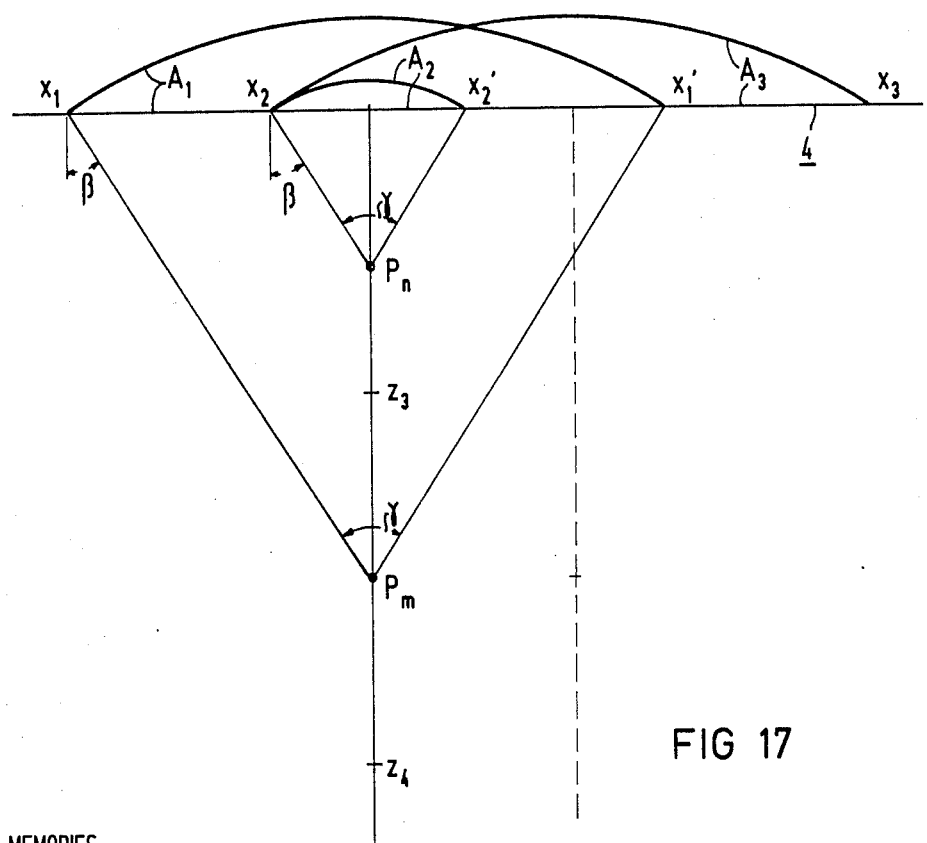
FIG. 17: an illustration of the acceptance of the correction values given a dynamic focusing system.

The adaption initially applies only to the depth region from which the measured values derive. Correction of focusings that do not lie in the measured depth region can also be undertaken with the set of correction curves for perpendicular and differently oblique sound incidence. This is illustrated with reference to FIG. 17, wherein corrected aperture is $A_1$ (between $x_1$ and $x_1'$). A dynamically focused array system will operate with an optimally depth-independent degree of focusing. For example, for the near range $z=0$ through $z=z_3$, it will operate with the smaller aperture $A_2$ (between $x_2$ and $x_2'$) and an adapted curvature. The aperture $A_2$ is selected such that the aperture angle $\phi$ of the object point ($P_m$ or $P_n$) is optimally constant. The angle for the oblique directions of incidence amounts to a maximum of $\beta$ independently of the aperture. Measured values that were acquired with the larger aperture are thus available for the correction of the transit-time errors of the smaller aperture. The correction value for $x_2$ of the small aperture having the oblique angle of incidences $\beta$ is thus found in the curve for the boundary value of the aperture $A_3$. This procedure can be analogously expanded to focusings in depths greater than $z_4$ as well.

Figure 18:
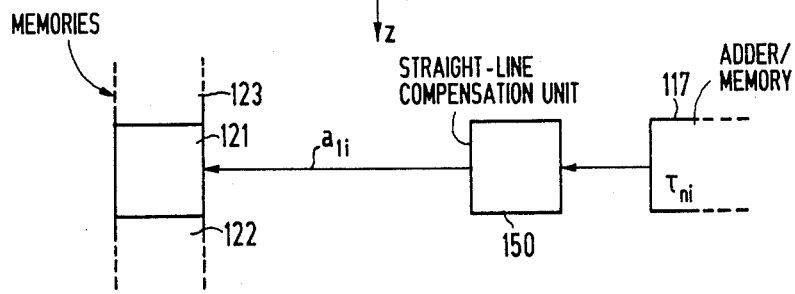
FIG. 18: an especially simple embodiment of the measured value identification on the basis of the formation of a compensation straight-line which can be utilized in FIG. 14.
Figure 19:
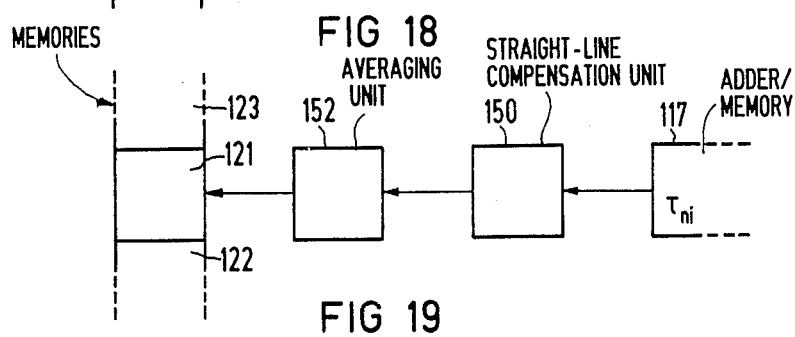
FIG. 19: an embodiment of the measured value identification according to FIG. 18 including an averaging.

An alternative is shown in FIG. 18 which can be utilized instead of the aligning unit 118 and the averaging unit 19 in the computer 134 according to FIG. 14. As described above in connection with FIG. 8, this alternative makes use of a compensation straight-line AG. The unit 150 shown in FIG. 18 is capable of placing a compensation straight-line AG through the values $\tau_{ni}(x)$ supplied by the adder/memory 117, and subsequently, of also defining the respective differences $a_{1i}$ from this compensation straight-line AG. The differential values $a_{1i}$ are supplied to the memories 121, 122, 123 ... for further processing in the above sense.

An averaging may also be carried out in a procedure according to FIG. 18. To this end, an averaging unit 152 is inserted between the output of the unit 150 and the memories 121, 122, 123, ...

Figure 20:
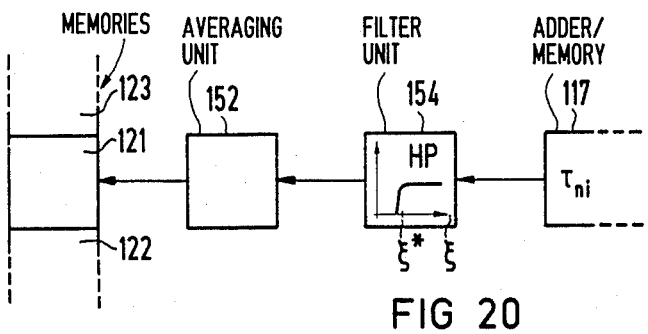
FIG. 20: an alternative embodiment of the measured value identification on the basis of a high-pass filtering.

A third alternative is shown in FIG. 20. In this embodiment, a high-pass filtering in the local region is carried out with a filter unit 154 between the adder/memory 117 and the averaging unit 152. The filter output is stored in a memory (not shown) which can be integrated in the filter unit 154. In other words, when the last curve $\tau_{7i}$ (in the example of FIG. 7) is filtered, all samples of the seven curves which are high-pass filtered, and had been stored up to then, are averaged in the averaging unit 152, in the fashion indicated in FIG. 7. The order of magnitude of the (spatial) corner frequency $\zeta^*$ in the high-pass filtering should lie at the reciprocal of the length of the overall reception aperture (for example, $E_{l7}$, $E_7$, $E_{r7}$). the overall reception aperture A unit such as 150 or 154 may be interposed between the units 117 and 118 in FIG. 14.

As mentioned above, the transit-time distortion curve can alternatively be measured by correlation of the respective signals from the elemental transducers with a sum signal of the focused reception aperture. An apparatus for this embodiment is shown in FIG. 21. A sum reception signal s of the summing unit 132 is supplied to a modified selection circuit 113a. The signal s then proceeds to the depth selector 114, and then to correlator 115. The correlator 115 is directly followed by the averaging unit 118. The distance of the correlation maximum M from the source 0 is taken from the correlator 115 as the measured value. This measured value is a measure for the transit-time distortion effective immediately at the elemental transducers, as was respectively acquired by integration in the methods set forth above. Further processing ensues as in FIG. 14.

In addition to the correction of the transmission focusing with the units 105 through 109, the selection can be undertaken in the embodiment of FIG. 21 in the adaptation beginning with the first iteration step as to whether correlation is to be undertaken with the uncorrected sum reception signal s', which is supplied by a summing unit 156 preceding the units 127, etc., or is to be undertaken with the corrected sum reception signal s from the summing unit 132 (arranged following the units 127, etc.). Both possibilities are provided in FIG. 21. A switch 158 within the measured value selection circuit 113a enables switching between the two possibilities.

The possible applications of the above-recited principle of the adaptive antenna are not limited to parallel scan, but can be transferred to conditions given a "curved array." The manner by which the method can be transferred to an electronic sector scan shall be set forth with reference to FIGS. 22 (A and B), 23 and 24.

First, the division of an array is far finer (for example, 0.5 wavelengths) for an electronic sector scan than for a linear array (for example, 1.5 wavelengths). The following Figures presume that enough elemental transducers are interconnected for the correction measurement following the width of the array and the focusing so that the same effective overall width of the elemental transducers arises as previously selected in the parallel scan.

Figure 22A:
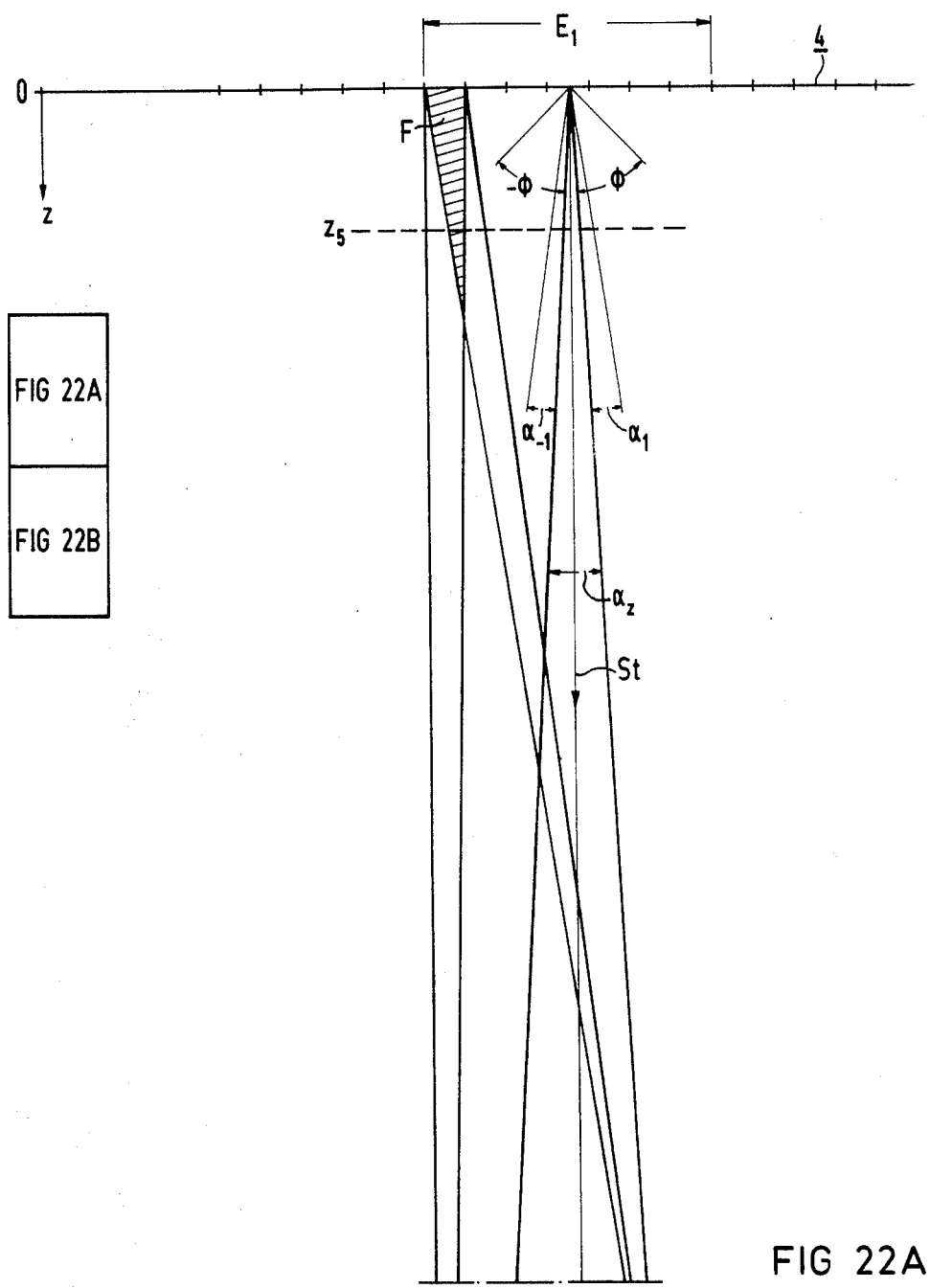
FIG. 22: a geometrical conditions in the sector scan.
Figure 22B:
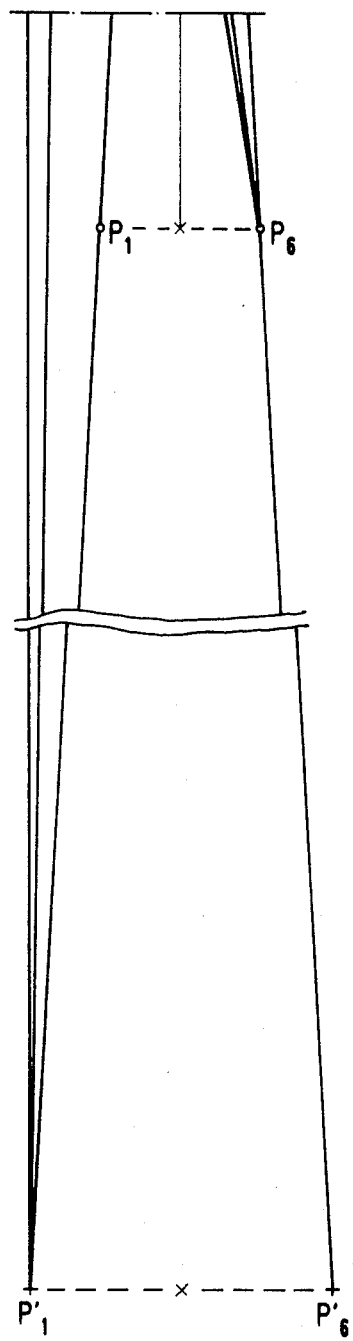

The geometrical relationships are shown in FIG. 22 when the same area size... as in the parallel scan is assumed for the signal acquistion region between $P_1$ ... $P_6$ and $P'_1$ ... $P'_6$. The two extreme return paths from $P_6$ and $P'_1$ yield an overlap (shaded area F) in the transducer-proximate region to the depth $z_5=0.5$ cm, this still being about half as wide at $z_5$ as at $z=0$. When such a measure is utilized as criterion for the maximally allowed size (width and depth) of the signal capture region (in parallel scan as well), a relationship between this region size and the depth position thereof, and the thickness of the measurable disturbing layer, is produced. As shown in FIG. 22, the number of scan lines allowed for averaging and the width of the directly measurable reception aperture $E_1$ are comparable in size to those in the parallel scan. In sector scan, however, the return travel distance given large pivot angles $\phi$ of, for example, $+45°$ or $-45°$ relative to the perpendicular, is at a far greater angle in the disturbing layer The value $z_5$ is thus diminished by the factor 0.707. A compromise which amounts to a shortening factor of about 0.8 suffices in practice.

Figure 23:
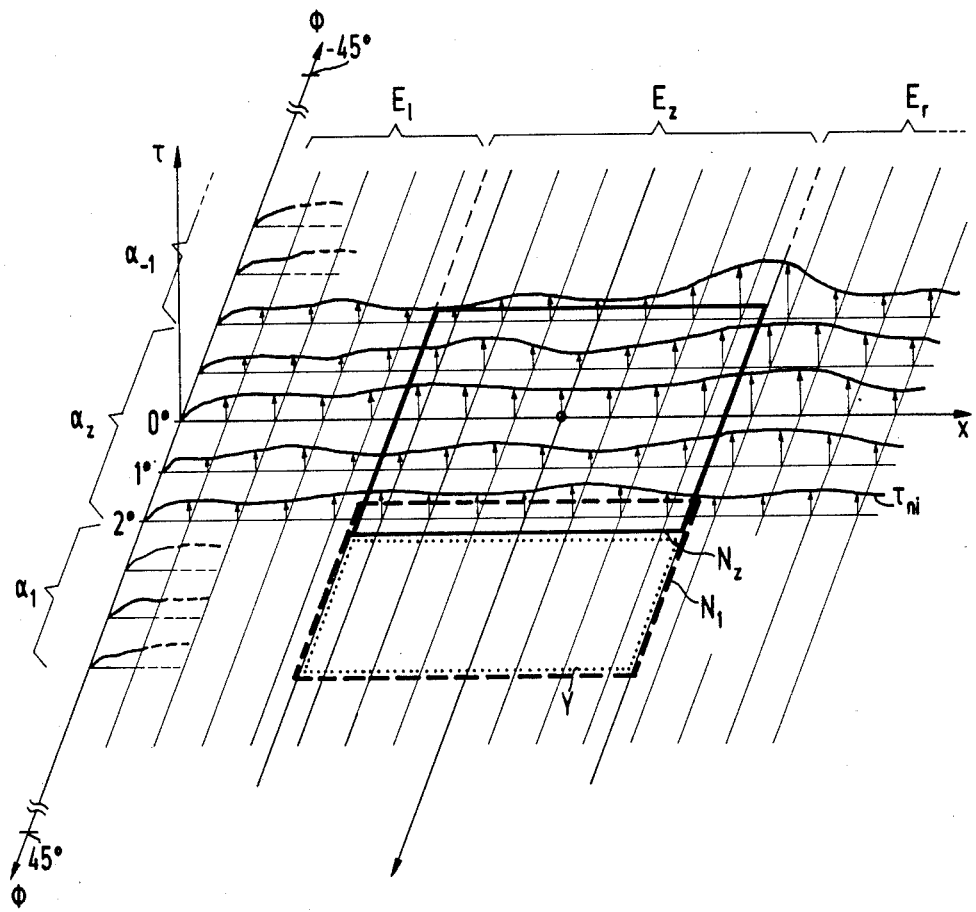
FIG. 23: the data field in the sector scan.

The signal processing postulates the standard performance features of an electronic sector scanner such as pivot and focusing in the transmission and reception cases, designed for a homogeneous transmission medium. The data sets for $\tau_{ni}$ illustrated in FIG. 23 are then obtained in the fashion set forth above for the parallel scan. The index n now refers to the number of the transmission beam direction with ascending deflection angles, and i references the transducer number on the array. Only the transmission beam directions inside the angular range $\alpha_z$ and the transducers within the reception aperture $E_1$ are to be "aligned" under one another and averaged with one another (see FIG. 22). This field $N_z$ is bounded by a thick line in FIG. 23. For a reception aperture larger than $E_l$, the curves referenced $E_l$ and $E_r$—upon retention of the "aligning" from the central region $E_z$—will then be averaged and employed in the region $\alpha_z$ in accord with the above explanations for parallel scan.

The data for the neighboring angular region $\alpha_1$ are acquired in the same way as for $\alpha_z$. The "aligning" of these regions with one another is not done here in the same fashion as in the case of parallel scan. The neighboring regions should therefore be selected overlapping, as indicated in FIG. 23 with the fields $N_l$ and $N_z$ shown with broken lines and with thick solid lines. The "new" region $\alpha_1$ thus begins the "aligning" with one to three curve sections of the region $\alpha_z$ brought into alignment with one another ("aligned") and averaged.

The averaging can be limited to adjacent regions, as symbolized by the area Y bounded with dot-dash lines.

Figure 24:
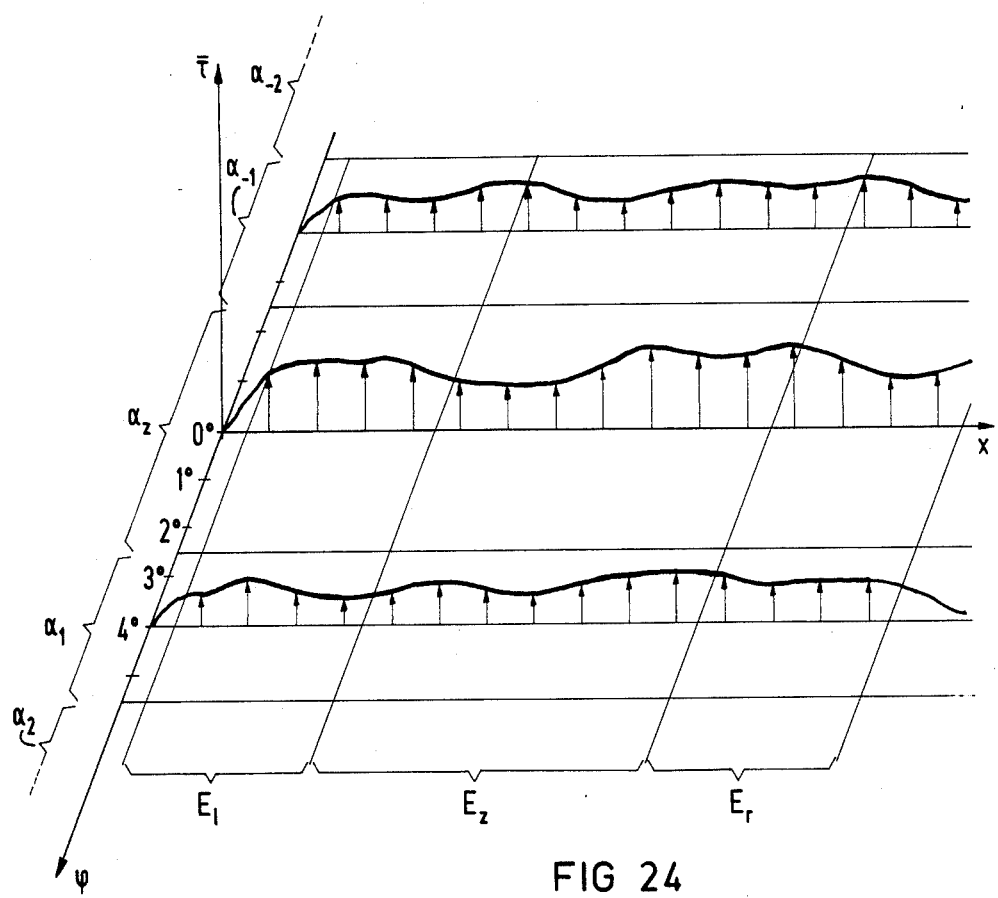
FIG. 24: averaged measured value curves given sector scan.

After the averaging, curves according to FIG. 24 are obtained, being valid for every angular range (i.e. $\alpha_z$, $\alpha_1$, $\alpha_{-1}$, $\alpha_2$, $\alpha_{-2}$, ...). For example, the curve section shown with a thick solid line applies for $\alpha_z$ in the region of $E_z$ and for the left and right edge regions $E_l$ and $E_r$ which proceed beyond $E_z$.

According to FIG. 14, the operation of an ultrasound B-scanner having adaptive antenna is as follows. The array 101 has a scan or button 160 connected thereto, which may be physically located on the control unit 133, with which the automatic adaption is initiated in every new scan position as long as the button 160 is pressed. The more scan runs which are to be executed for averaging the longer the button 160 is pressed. The operator slightly tilts the array 101 during the adaption. The shortest possible time for the adaption amounts to about 120 ms when three transmission foci are provided for the depth of the signal capture region. In the iteration, the correction values identified in the preceding adaption step are used for the following transmission phase within the adaption in order to improve the transmission focus. The aperture (during reception and/or transmission) can thereby increase from a smallest to a largest value.

After the adaption, a normal, fast scan can be carried out in the examination phase as long as the sectional plane is not too greatly modified so that noticibly different paths in the subcutaneous fatty tissue are traversed. The method is thus also fundamentally suited for the portrayal of the heart. The tilting of the scan plane in the adaptation phase is then superfluous due to the self-motion of the heart.

For matching to the specific conditions of an application, the thickness of the belly fat layer and the maximum depth position of the back boundary $P'_1$, $P'_6$ of the signal capture region can be entered at the terminal of the scanner based on the visual impression. The computer 134 determines the position and size of the signal acquisition region $P_1 \ldots P_6$ through $P'_1 \ldots P'_6$ therefrom according to the above-specified criteria (overlapped degree of the return paths).

Although modifications and changes may be suggested by those skilled in the art it is the intention of the inventors to embody within the patent warranted hereon all changes and modifications as reasonably and properly come within the scope of their contribution to the art.

We claim as our invention:

1. A method for generating an ultrasound B-image of an examination subject having acoustic inhomogeneities using an ultrasound array having a plurality of transducer elements, each transducer element having a variable delay associated therewith, including a delay used for a standard focusing of said ultrasound array, said method comprising the steps of:
    scanning a sectional plane of said examination subject with focused ultrasound beams from said ultrasound array in an adaptation phase;
    measuring, in said adaptation phase, echo signals reflected by said examination subject using a selected active aperture, said echo signals being disturbed by the acoustic inhomogeneities in said examination subject;
    calculating correction values for the delay of each of said element in said ultrasound array from the delays used for said standard focusing based on the measured values obtained in said adaptation phase; and
    scanning said examination subject with said ultrasound array using the delays calculated based on said correction values and the delays used for said standard focusing to compensate for said disturbances caused by said acoustic inhomogeneities to obtain further echo signals; and
    generating a standard B-image from said further echo signals.

2. A method as claimed in claim 1, wherein the step of calculating said correction values is further defined by cross-correlation the echo signals from said transducer elements of said ultrasound array.

3. A method as claimed in claim 2, wherein the step of cross-correlating is further defined by cross-correlating echo signals of two neighboring transducer elements in said ultrasound 4. A method as claimed in claim 2, wherein the step of cross-correlating is further defined by the steps of:
    grouping said transducer elements of said ultrasound array into a plurality of groups; and
    cross-correlating the echo signals from neighboring groups of transducers in said ultrasound array.

5. A method a claimed in claim 2, wherein the step of calculating said correction values is further defined by the steps of:
    identifying the time shift value of the maximum of said cross-correlation;
    generating a distribution of transit-time differences by comparing said time shift value to an expected value for a homogeneous examination subject; and
    after scanning the entirety of said sectional plane, deriving said measuring values from said distribution and calculating said correction values therefrom.

6. A method as claimed in claim 1, wherein the step of calculating said correction values is further defined by calculating correction values by averaging.

7. A method as claimed in claim 6, comprising the additional step of tilting said ultrasound array with respect to said examination subject in said adaptation phase.

8. A method as claimed in claim 5, comprising the additional step of:
    aligning the time shift values from said transducer elements when calculating said correction values; and
    subsequently averaging said correction values.

9. A method as claimed in claim 1, wherein said adaptation phase is repeated through a selected number of iterations, with the correction values obtained from one iteration being used for transmitting said ultrasound beams in an immediately following iteration.

10. An apparatus for generating an ultrasound B-image of an examination subject having acoustic inhomogeneities comprising:
- an ultrasound array having a plurality of transducer elements, each transducer element having means connected thereto for variably setting a delay for that transducer, including a delay for standard focusing of said ultrasound array;
- means for scanning said examination subject with ultrasound beams generated by said ultrasound array with said delays for standard focusing;
- means for processing ultrasound echo signals reflected by said examination subject using a selected active aperture and for generating a standard B-image therefrom;
- means for scanning a sectional plane of said examination subject with focused ultrasound beams from said array in an adaptation phase;
- means for measuring echo signals reflected by said examination subject in said adaptation phase disturbed by the acoustic inhomogeneities in said examination subject;
- means for calculating correction values for the delay of each element in said ultrasound array from the delays used for said standard focusing based on the measured values obtained in said adaptation phase; and
- means for scanning said examination subject with said ultrasound array based on said correction values and the delays used for said standard focusing for compensating for said disturbances caused by said acoustic inhomogeneities.

11. An apparatus as claimed in claim 10, wherein said means for calculating said correction values is a means for cross-correlating the echo signals from said transducer elements of said ultrasound array.

12. A apparatus as claimed in claim 11, wherein said means for cross-correlating is a means for cross-correlating echo signals of two neighboring transducer elements in said ultrasound 13. An apparatus as claimed in claim 11, further comprising means for grouping said transducer elements of said ultrasound array into a plurality of groups, and wherein said means for cross-correlating is a means for cross-correlating the echo signals from neighboring groups of transducers in said ultrasound array.

14. An apparatus as claimed in claim 11, wherein said means for calculating said correction values comprises:
- means for identifying a time shift value of the maximum of the output of said means for cross-correlating;
- means for generating a distribution of transit-time differences including means for comparing said time shift value to an expected value for an homogeneous examination subject; and
- means for deriving said measured values from said distribution and for calculating said correction values therefrom.

15. An apparatus as claimed in claim 10, wherein said means for calculating said correction values includes means for averaging.

16. An apparatus as claimed in claim 15, wherein said means for calculating said correction values includes means for aligning added time shift values from said transducer elements when calculating said correction values and means for subsequently averaging said correction values after aligning.

17. An apparatus as claimed in claim 10, further comprising means for tilting said ultrasound array with respect to said examination subject in said adaptation phase.

18. An apparatus as claimed in claim 10, further comprising control means for repeating said adaptation phase through a selected number of iterations, with the correction values obtained for one iteration being used for transmitting said ultrasound beams in an immediately following iternation.

19. An apparatus as claimed in claim 10, further comprising means for averaging a plurality of scans of said examination subject, and means for selectively varying the duration of said adaptation phase to control the number of scans used in said means for averaging.

20. An apparatus as claimed in claim 10, further comprising means for selecting the depth region in said examination subject from which said echo signals are reflected.

* * * * *